United States Patent [19]

Papisov et al.

[11] Patent Number: 5,582,172
[45] Date of Patent: Dec. 10, 1996

[54] SYSTEM OF DRUG DELIVERY TO THE LYMPHATIC TISSUES

[75] Inventors: Mikhail I. Papisov, Boston; Thomas J. Brady, Winchester, both of Mass.

[73] Assignee: The General Hospital Corporation, Boston, Mass.

[21] Appl. No.: 375,188

[22] Filed: Jan. 18, 1995

Related U.S. Application Data

[63] Continuation of Ser. No. 917,707, Jul. 21, 1992, abandoned.

[51] Int. Cl.$^6$ ............................................. A61B 5/055
[52] U.S. Cl. .................................. 128/653.4; 128/653.2; 128/654; 604/20; 424/1.25; 424/1.33; 424/1.65; 424/1.69; 424/1.73
[58] Field of Search ........................... 128/653.1, 653.2, 128/654, 659, 653.4; 604/20; 424/1.1

[56] References Cited

U.S. PATENT DOCUMENTS

| | | | |
|---|---|---|---|
| 4,126,669 | 11/1978 | Rothman | 128/654 |
| 4,310,505 | 1/1982 | Baldeschweiler | 424/1 |
| 4,311,688 | 1/1982 | Burchiel | 128/659 |
| 4,735,210 | 4/1988 | Goldenberg | 128/654 |
| 4,735,796 | 4/1988 | Gordon | 128/654 |
| 4,827,945 | 5/1989 | Gomon | 128/653 |
| 4,985,233 | 1/1991 | Klaveness et al. | 128/654 |
| 5,021,236 | 6/1991 | Gries | 128/654 |
| 5,023,072 | 6/1991 | Cheng | 128/654 |
| 5,101,827 | 4/1992 | Goldenberg | 128/654 |
| 5,362,478 | 11/1994 | Desai | 128/654 |

FOREIGN PATENT DOCUMENTS

| | | |
|---|---|---|
| WO90/14846 | 12/1990 | WIPO. |
| WO94/05203 | 3/1994 | WIPO. |

OTHER PUBLICATIONS

Papisov, et al., Sixth Int. Symposium on Rec. Adv. In Drug Delivery Systems, Feb. 1993 (Abstract).
Molea et al., European Association of Nucl. Medic. Congress, (1992), (Abstract).
Weissleder, *Magnetic Resonance in Medicine*, 22:209–212, (1991).
Papisov, et al., "Colloidal Magnetic Resonance Contrast Agents: Effect of Particle Surface on Biodistribution", *J. Magn. Mater*, 122:1–3 (1993), (Abstract).

*Primary Examiner*—Randall L. Green
*Assistant Examiner*—Chalin Smith
*Attorney, Agent, or Firm*—Fish & Richardson P.C.

[57] ABSTRACT

A substance for diagnosis or therapy of an animal. The substance includes an agent which is detectable or therapeutically active, the agent being linked to a carrier which is linked to a targeting site, whereby the agent accumulates in the lymphatic system of the animal to a greater degree than if the targeting site were absent.

36 Claims, 6 Drawing Sheets
(2 of 17 Drawing(s) in Color)

SYSTEM OF DRUG DELIVERY TO THE LYMPHATIC TISSUES

This is a continuation of application Ser. No. 07/917,707, filed Jul. 21, 1992, now abandoned.

The invention relates to diagnostic or therapeutic substances for delivering diagnostic and therapeutic agents to an area of interest, e.g., the lymphatic system.

BACKGROUND OF THE INVENTION

It is well known that the lymphatic tissues are involved in most pathological processes. They are highly responsive even to minor disturbances in the surrounding tissues and represent a sensitive indicator of disease. The status of lymph nodes is especially important in cases of severe disease, such as metastatic cancer, where detection and accurate lymph node staging are essential to successful therapy. While histopathology is in many cases the most accurate method of lymph node assessment, this approach requires a surgical procedure and is limited to regional anatomic sites. Current techniques in medical imaging often use size criteria to assess tumor involvement of a lymph node. However, size is an imperfect indicator since normal-sized nodes may contain cancer while enlarged nodes may be cancer-free. Therefore, diagnostic preparations that selectively highlight the details of lymph node structure and function could improve both the sensitivity and specificity of major modern diagnostic methods, such as nuclear medicine, magnetic resonance imaging, and x-ray computed tomography. The efficacy of therapy, in turn, may be dramatically improved by increasing the local concentration of a drug in the injured tissue. Agents that can reach all lymph nodes after a single intravascular injection are preferable because of the large number of lymph nodes in the human body and difficult access to most of them.

The structure of the lymphatic system allows drug delivery to the lymph nodes by drainage of an interstitially localized preparation through the lymphatic vessels. This route has been adopted for the lymphography and imaging of the peripheral lymph nodes and has recently been suggested for administration of therapeutic preparations, such as anticancer agents immobilized on dextran molecules or on colloidal carbon particles.

Previously, preparations, including carbohydrates and their derivatives, have been delivered to the lymph nodes by local (interstitial or intralymphatic) administration. The behavior of locally administered preparations in the lymphatic system depends on the type of preparation. For example, while colloids are often taken up from the lymph by the lymph node cells, some polymeric preparations, such as dextran, can pass through lymph nodes via the lymphatic sinuses without significant uptake. After intravascular administration, a major fraction of many conventional preparations are taken up by the liver and spleen rather than by lymphatic tissues. The polymeric preparations show some uptake by the lymphatic system, but the lack of their accumulation in the lymph node tissue renders them less desirable as targeted diagnostic or therapeutic substances. These preparations, therefore, are likely useful for investigation of the lymph nodes located in easily accessible surface areas of the organism, but not for lymph nodes located in less accessible areas.

Despite the absence of significant accumulation in the lymphatic tissues after intravascular administration, previous preparations were used in biological models for lymph node investigation. Metalloporphyrins have been used for the delivery of a radionuclide to the lymph nodes but the total amount of the isotope delivered to the lymph nodes did not usually exceed about 1%. It has also been shown in Weissleder, R. et al., "Ultrasmall Supermagnetic Iron Oxide: Pharmacokinetics and Toxicity", American Journal of Radiology, 1989, Vol. 152, pp. 167–73, that a minor fraction (about 3.6% of the dose/gram of tissue) of previous preparations of ultra-small iron oxide particles appeared in the lymphatic tissues after intravascular injection but the majority of these particles are found in the liver and spleen. Only minimal amounts of the particles were detectable in lymph nodes and other tissues. Iron oxide particles may be used for magnetic resonance in imaging as discussed in U.S. Pat. Nos. 4,770,183 and 4,827,945, and for producing contrast images of tissue including lymph node tissue.

Macromolecular drug complexes have been intensively studied as prototypes of parenteral diagnostic and therapeutic preparations. They typically consist of a carrier (e.g., polymeric molecules, vesicles, and microparticles) and agent molecules attached or incorporated therewith. The role of a carrier is to alter the biodistribution of an agent, to increase its concentration in a desirable target tissue, and to decrease its concentration in non-target sites thereby suppressing side effects. To provide accumulation of a drug complex in a target site, molecules possessing a high affinity to target tissue are often used as components of a carrier. Antibodies or their fragments, and receptor ligands (e.g., hormones or their analogues) are common examples of high affinity molecules used in targeted drugs.

Drug targeting, as a pharmacokinetic concept, is generally based on the postulate that the agent should not significantly affect the pharmacokinetics or the biodistribution of the carrier. However, certain agents are able to interact with plasma or cell surface components, and can cause a dramatic difference between the biodistribution of the carrier and the drug complex.

Once the drug complex has accumulated in the targeted tissue, the behavior of the agent depends on the method of its attachment or incorporation with the carrier.

The appearance of minor fractions of intravascularly administered substances in the lymph nodes has been reported for a diverse group of polymers and colloids (e.g., polyvinyl alcohol, iron dextran, dextran, liposomes). These substances were seldom found in the lymph node cells, other than in the macrophages or mast cells and their uptake by the lymph nodes was insignificant. Similar cells are responsible for the uptake of these substances in the liver, spleen, bone marrow, kidney and other organs.

SUMMARY OF THE INVENTION

In general, the invention features, a substance for diagnosis or therapy of an animal, e.g., a fish, a reptile or a mammal, e.g., a rodent, e.g., a mouse or rat, or rabbit or a human, including, an agent which is detectable or biologically, e.g., therapeutically, active, the agent being linked to or held within a carrier which includes or is linked to a targeting site, whereby the agent accumulates in the lymphatic system, e.g., in a lymph node, of the animal to a greater degree than if the targeting site were absent.

In preferred embodiments, the diameter of the substance, molecule or particle is less than 100 nm. More preferably, the diameter, e.g., the hydrated diameter, of the substance is between 10 and 30 nm.

In preferred embodiments: the carrier includes a polymer, e.g., a linear or non-linear, polymer; the polymer is chosen from the group of polypeptides, polysaccharides, and copolymers thereof; the polymer includes polylysine, e.g., a polylysine copolymer; the polymer includes a polyglycosylated synthetic or natural polymer; the polymer includes silicon or phosphorous, or both.

In preferred embodiments the targeting site is capable of binding C3 or a naturally occurring variant or fragment of C3, e.g., the targeting site includes polyvinyl alcohol, glycerol, and sulphur containing molecules, e.g., cysteine.

In preferred embodiments, the targeting site comprises a carbohydrate.

In preferred embodiments, the carbohydrate molecule is chosen from the group of dextran, starch, beta-glucan, glucose, Ficoll (the trade name for a synthetic polymer of sucrose) and their derivatives and analogues; and the carbohydrate has a molecular weight from 1 to 20 Kilodaltons (kD).

In preferred embodiments, the polymer includes a functional group for linking the carrier to the agent; the functional group includes an amino group; the functional group includes an amino group derivative; the functional group includes a carboxylic group; the functional group includes a carboxylic group derivative; the functional group includes a carbonyl group; the functional group includes a carbonyl group derivative; the functional group includes a thiol group; the functional group includes a thiol group derivative; the functional group includes an aromatic; the functional group includes an aromatic derivative; the functional group includes a halogen; the functional group includes a chelate; the functional group includes a chelate derivative; the functional group includes an Noxysuccinimide ester.

In the preferred embodiments, the carrier includes a particle; the carrier includes an aggregate of particles; the carrier includes a colloid; the carrier includes a colloidal particle; the particle includes a functional group for linking the particle to the agent; the particle includes an organic particle; the particle includes an inorganic particle; the particle includes a composition of organic particles; the particle includes a composition of inorganic particles; the particle includes latex; the particle includes iron; particle includes iron oxide, the particle includes silicon; the particle includes a radioactive isotope, e.g., any of indium, technetium, iodine, gallium; and the particles consist of agent.

In the preferred embodiments, the agent includes a magnetic label, e.g., a paramagnetic or superparamagnetic label; the magnetic label is chosen from the group of iron, e.g., iron oxide or ferrite, gadolinium, manganese, and dysprosium; the agent includes a stable isotope, e.g., an isotope chosen from the group of phosphorous, silicon, and sodium, having nuclear magnetic resonance properties; the agent includes a biologically active component e.g., a radioactive isotope, e.g., an alpha or beta emitter, e.g., a radioactive isotope chosen from a group of I, Bi, and Au; the agent includes superparamagnetic iron oxide; the agent includes a peptide, e.g., an enzyme; the agent is a toxin, hormone, inhibitor, and antineoplastic or antibiotic agent.

In preferred embodiments, the diameter of the carrier is less than or equal to 100 nm. More preferably the diameter, e.g., the hydrated diameter, of the carrier is bhetween 10–30 nm.

In preferred embodiments the diagnostic or therapeutic substance includes a plurality of targeting sites, wherein the targeting sites are distributed on the carrier such that when the substance is injected intravascularly into an animal e.g., a rat or rabbit at a dosage of 1 mg per 1 kg body weight of the animal, at least 5% of the injected dose of the substance per gram of lymph node tissue accumulates in a lymph node.

In preferred embodiments the diagnostic or therapeutic substance includes a plurality of targeting sites, the targeting sites being distributed on the substance such that when the substance is exposed to rat blood plasma containing 1 mM sodium citrate for two hours at 37° C., more than 80% of the protein absorbed to the substance is C3 or its naturally occurring variants.

In preferred embodiments the diagnostic or therapeutic substance includes a plurality of targeting sites, the targeting sites being distributed on the substance such that when exposed to rat plasma containing 1 mM sodium citrate for 2 hours at 37° C. the substance absorbs less than 50% of its weight in blood plasma proteins.

In preferred embodiments the diagnostic or therapeutic substance includes a plurality of targeting sites, said targeting sites being distributed on the substance such that when the substance is exposed to rat plasma containing 1 mM sodium citrate for two hours at 37° C., greater than 80% of the protein absorbed to the substance is C3 or its naturally occurring variants and the substance absorbs less than 50% of its weight in blood plasma proteins.

In preferred embodiments the diagnostic or therapeutic substance includes a plurality of targeting sites, the targeting sites being distributed on the substance such that when the substance is exposed to rat plasma containing 1 mM sodium citrate for 2 hours at 37° C. the substance binds less than 1 molecule of transferrin per particle of said substance; 0.01–1.0 mg/ml mixture of the substance in a 0.9% NaCl in water solution will not aggregate or precipitate during the first 24 hours of incubation after the substance is added to the solution when incubated at 25° C.; a 0.01–1.0 mg/ml mixture of the substance in 0.9% NaCl in water solution will not aggregate or precipitate during the first 72 hours of incubation after the substance is added to said solution when incubated at 37° C. in a homogenous magnetic field at 0.47 Tesla.

In another aspect, the invention features a method of preparing a diagnostic or therapeutic substance including: supplying a carrier comprising a target site, e.g. carbohydrate; linking the agent with the carrier; and linking the agent with the targeting site In preferred embodiments, the carrier is a polymer or a particle; the agent is a radioactive compound or a contrast agent; an organic molecule is linked to the carrier.

In another aspect, the invention features a pharmaceutical composition comprising a diagnostic or therapeutic substance of the invention and a pharmaceutically acceptable compound, e.g., a vehicle.

In another aspect, the invention features a method of studying, e.g., imaging, a tissue or organ, or organ system, e.g., the lymphatic system, e.g., lymph nodes, comprising: supplying a diagnostic or therapeutic substance of the invention; administering, e.g., injecting, e.g., intravascularly injecting, the diagnostic or therapeutic substance to an animal, e.g., a reptile or a mammal, e.g., a rodent, e.g., a mouse or rat, or a rabbit or a human; and determining or detecting the distribution of the diagnostic or therapeutic substance in the animal.

In preferred embodiments, the determination or detection of distribution is made by gamma-scintigraphy, photon emission tomography, magnetic resonance imaging, magnetometry, or magnetometric imaging.

In another aspect, the invention features a method of treating an animal, e.g., a fish, a reptile or a mammal, e.g., a rodent, e.g., a mouse or rat, or a rabbit or a human with a disorder or disease of the lymphatic system including administering, e.g., injecting, e.g., intravascularly injecting, to the animal a diagnostic or therapeutic substance of the invention.

In preferred embodiments the agent of the substance is chosen from the group of chemotherapeutic, agents for hyperthermia, radiotherapeutic, enzyme therapeutic, immunotherapeutic.

In another aspect, the invention includes a method obtaining a magnetic resonance image including: supplying a diagnostic or therapeutic substance of the invention; administering the diagnostic or therapeutic substance to an animal; and imaging the animal to determine the distribution of the diagnostic or therapeutic substance.

In preferred embodiments the imaging is performed 1, 2, 7, 15, 30, 37, or 45 or more days after administering the diagnostic or therapeutic substance.

In another aspect the invention includes a method of delivering an agent to the lymphatic system, e.g., to the lymph nodes, of an animal, e.g., a fish, a reptile or a mammal, e.g., a rodent, e.g., a rat or mouse, or a rabbit, or a human, by supplying a diagnostic or therapeutic substance of the invention and administering, e.g., intravascularly injecting, the diagnostic or therapeutic substance to the animal.

In another aspect, the invention includes, a method of delivering an agent to a site of inflammation in an animal, e.g., a fish, a reptile or a mammal, e.g., a rodent, e.g., a rat or mouse, or a rabbit, or a human, including: supplying a diagnostic or therapeutic substance of the invention and administering, e.g., intravascularly injecting, said diagnostic or therapeutic substance to the animal.

In another aspect, the invention includes a method of identifying a site of inflammation in an animal, e.g., a fish, a reptile or a mammal, e.g., a rodent, e.g., a rat or mouse, or a rabbit, or a human, including: supplying a diagnostic or therapeutic substance of the invention, administering, e.g., intravascularly injecting, the diagnostic or therapeutic substance to the animal and determining or detecting the distribution of the diagnostic or therapeutic substance.

In another aspect, the invention features a substance (e.g, a carrier) for diagnosis or therapy of an animal, the substance including a carrier which includes a targeting site, whereby the carrier accumulates in the lymphatic system of the animal to a greater degree than if the targeting site were absent.

In preferred embodiments the substance includes a plurality of targeting sites, wherein the targeting sites are distributed on the carrier such that when the substance is injected intravascularly into said animal at a dosage of 1 mg per 1 kg body weight of the animal at least 5% of the injected dose of said substance per gram of lymph node tissue accumulates in at least one lymph node; the substance includes a plurality of targeting sites, the targeting sites being distributed on the substance such that when the substance is exposed to rat blood plasma containing 1 mM sodium citrate for two hours at 37° C., more than 80% of the protein absorbed to the substance is C3 or its naturally occurring variants; the substance includes a plurality of targeting sites, the targeting sites being distributed on the substance such that when exposed to rat plasma containing 1 mM sodium citrate for 2 hours at 37° C. the substance absorbs less than 50% of its weight in blood plasma proteins; the substance a plurality of targeting sites, the targeting sites being distributed on the substance such that: when the substance is exposed to rat plasma containing 1 mM sodium citrate for two hours at 37° C., greater than 80% of the protein absorbed to the substance is C3 or its naturally occurring variants and the substance absorbs less than 50% of its weight in blood plasma proteins.

The term "carrier" refers to a macromolecule, e.g., a polymer, or a colloidal particle, capable of incorporating, e.g., capable of being linked to an agent or capable of containing or holding an agent and which includes or can be linked to a targeting site.

The term "carbohydrate" refers to: (A) carbohydrates, i.e. substances described by the formula $[C(H_2O)]_m$, wherein "m" is equal to or greater than 2 and compounds containing one or more units of $[C(H_2O)]$; (B) their derivatives, e.g., dextran, i.e. substances that could be produced by oxidation, reduction, substitution, elimination, hydrolysis, polymerization, condensation, rearrangement or other reactions involving any one or more functional groups, atoms or bonds of carbohydrates, e.g., monosaccharides, oligosaccharides, polysaccharides, and natural, chemically changed, and fully synthetic compound; and (C) a fragment of a compound of group (A) or (B) containing a group or fragment of a compound of group (A) or (B), e.g., OH-group, glycol group, hemiacetal group, or combination of the above groups.

The term "graft" refers to an association of covalent, noncovalent, or covalent and noncovalent bonds.

The term "core" refers to the inner part of a carrier (e.g., molecule, particle, microsphere, microcapsule, vesicle, or combination thereof) excluding the targeting site or sites.

The term "carbohydrate-grafted carrier" refers to any carrier comprising a core linked, e.g., grafted, to carbohydrate molecules which form the targeting site.

The term "agent" refers to detectable agents e.g., diagnostic agents (i.e., substances useful in diagnostic methods, e.g. radionuclides, para- ferro- and superparamagnetic substances) and biologically active agents, e.g., therapeutic compounds.

The term "protected carrier" refers to carriers having a core and agent transported therein protected (e.g., sterically) by grafted carbohydrate molecules from interaction with a cell or a protein of an animal to which they are administered.

The term "targeting site" refers to a site on the carrier which includes a carbohydrate and/or is capable of binding to C3 (the third component of complement) or a naturally occurring fragment or variant of C3.

The term "biologically active" refers to substances that are able to affect biological systems including, e.g., therapeutic agents and inorganic and organic compounds.

It has been found that macromolecular and colloidal complexes which include a targeting site preferably a plurality of targeting sites, e.g., an outer carbohydrate structure, or other structures which can interact with C3, allow for efficient delivery of the intravascularly administered complex to the lymphatic tissues. While not being bound by theory, it appears that the targeting sites, e.g., of carbohydrate-grafted (e.g., dextran-grafted) polymers and colloidal particles of the invention avoid recognition in the liver and bone marrow, but are readily taken up in the lymph nodes. This behavior allows an effective transfer process resulting in localizing intravascularly administered preparations in lymph nodes.

Carbohydrates, which are believed to be responsible for the carrier accumulation in the lymph nodes, may by themselves have no affinity to the lymph node tissue and may accumulate or may not accumulate by themselves in a considerable amount in the lymph nodes after intravascular administration. However they can form the targeting site of a carrier which is responsible for accumulation in the carrier in the lymphatic tissue. While not being bound by theory, it is possible that interactions of a carbohydrate with C3 or its naturally occurring fragments or variants of C3 play a significant role in the biodistribution of the diagnostic and therapeutic substances of the invention. Therefore, substances other than carbohydrate capable of interacting e.g., binding or associating, with C3 and occurring fragments or variants of C3 may be used as a targeting member of the invention. Therefore, the approach used in this invention differs from commonly used delivery systems targeted by delivery with high-affinity molecules.

Agent carriers of this invention are grafted by carbohydrate molecules (which form a target site) which allow efficient targeted delivery of the intravascularly administered complex to the lymphatic tissues. The carbohydrate-grafted agent carriers are designed to deliver a wide range of diagnostic and/or therapeutic agents to lymphatic tissue preferably in a protected (e.g., sterically) complex.

The inner part of the carrier includes a structure of molecules or colloidal particles that carry diagnostic and/or therapeutic agents. The targeting site, in addition to its transporting function, may protect the inner part of the carrier against interaction with cell surface proteins and opsonizing proteins in blood.

The diagnostic and biologically active or therapeutic substances of the invention include macromolecular, e.g., polymeric, or particulate complexes and composites formed by grafting, e.g., linking, or incorporating agents into a carrier. The diagnostic and biologically active or therapeutic substances of the invention can thus deliver the agents to the lymph nodes after intravascular administration for diagnosis or/and therapy of lymphatic tissues.

The invention is useful for the diagnosis, treatment and prevention of lymphatic diseases and disorders (e.g., lymphatic metastases of cancers, lymphomas, lymph node hyperplasia etc.); for differentiation of the above diagnoses; for studying the structure and function of the lymphatic system; for immunomodulation or immunization; and for ecological monitoring.

The invention provides diagnostic and biologically active or therapeutic substances based on intravascular administration of soluble polymeric or colloidal complexes (composites) exhibiting biological properties which make them suitable for delivery of diagnostic and biologically active or therapeutic agents to lymphatic tissues. The invention includes polymeric and colloidal agent carriers that accumulate after intravascular administration in the lymphatic tissues, mainly in macrophage-populated areas, and the use of these carriers for in vivo delivery of diagnostic and biologically active or therapeutic agents to lymphatic tissues, particularly lymph nodes.

Other features and advantages of the invention will be apparent from the following description of the preferred embodiments and from the claims.

DETAILED DESCRIPTION

The drawings are first briefly described. The file of this patent contains at least one photograph executed in color. Copies of this patent with color photograph(s) will be provided by the Patent and Trademark Office upon request and payment of the necessary fee.

DRAWINGS

Figure 8A:
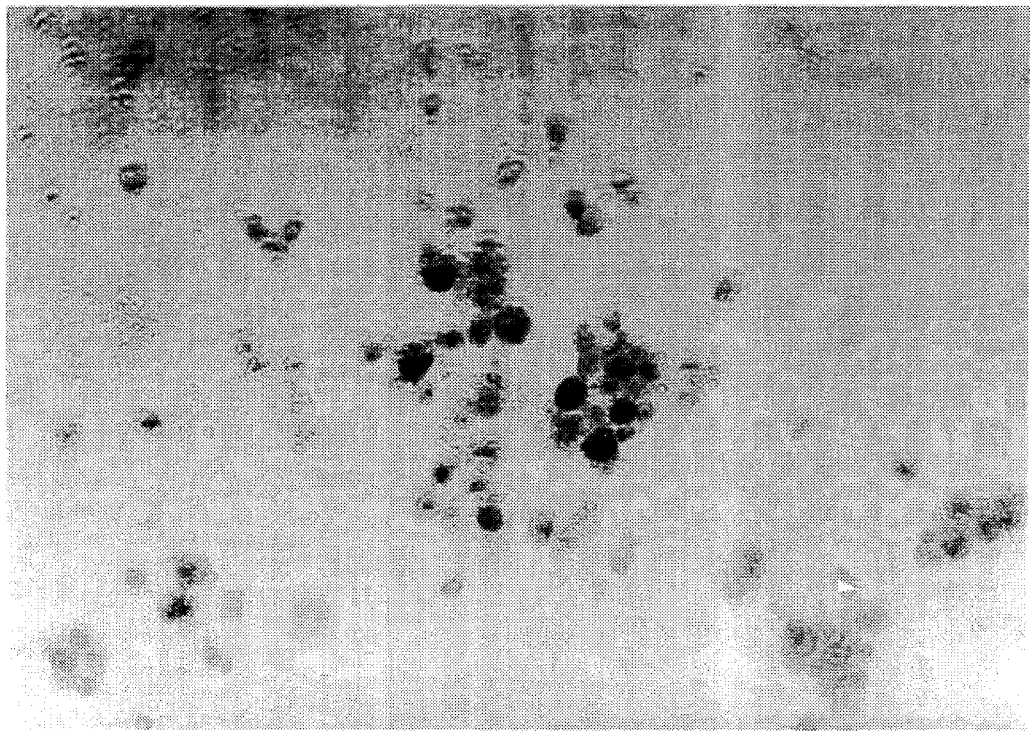
Figure 8B:
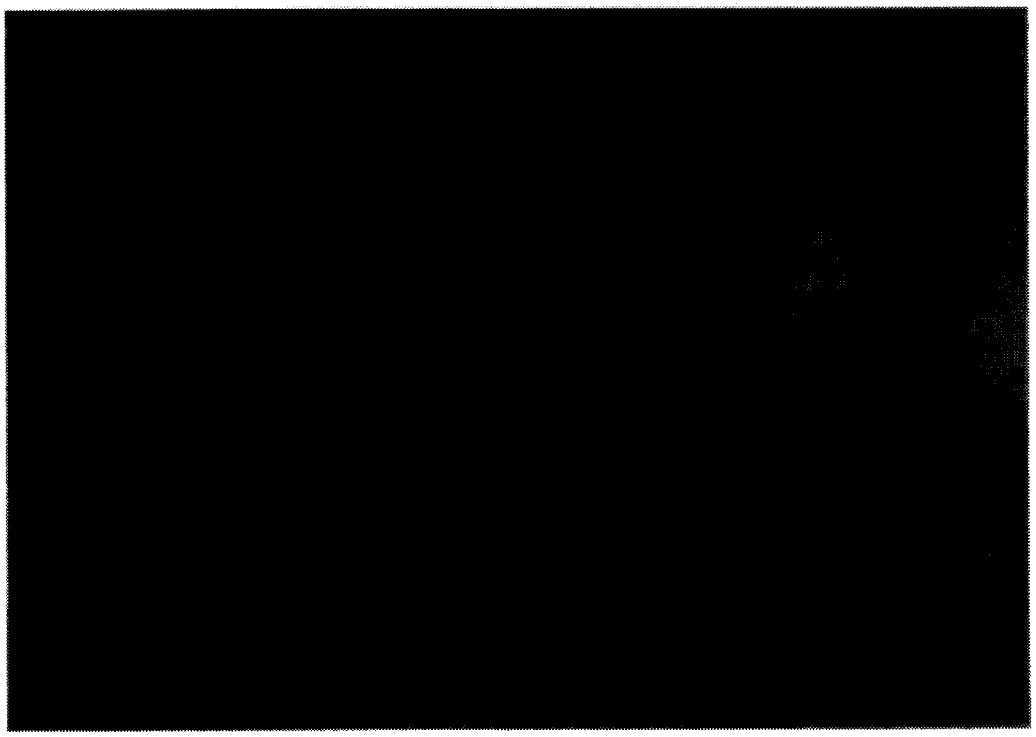
Figure 9A:
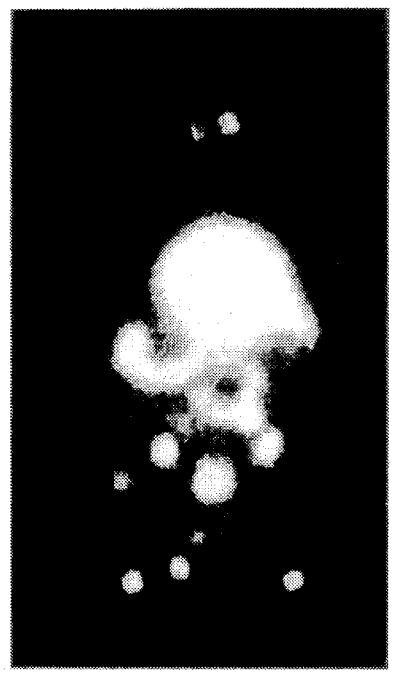
Figure 9B:
Figure 10A:
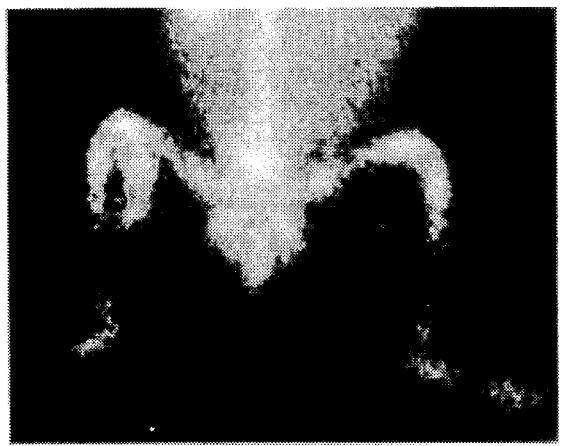
Figure 10B:

FIGS. 8a and 8b are photographs (magnification 400×) of the comparative disposition in the same area of lymph node tissue of a particle-based preparation, prepared according to Example 13 and administered 37 days before lymph node dissection (see FIG. 8a) and a polymer-based preparation, prepared according to Example 7, administered into the same animal 24 hours before dissection (see FIG. 8b);

FIGS. 9a and 9b are photographs of the frontal and lateral, respectively, whole body scintigrams of a rat 24 hours after intravenous injection of an indium labeled, Rhodamine X—loaded preparation prepared according to Example 8; and FIGS. 10a and 10b are photographs of the γ-images of animals with induced inflammation (rabbit) and adenocarcinoma (rat), respectively, 24 hours after administration of the preparation prepared according to Example 8.

Lymphatic Tissue

After intravascular administration, a fraction of macromolecules circulating in the blood slowly penetrate through endothelium into the interstitial space. If not retained in the interstitial space, the macromolecules are drained by the lymphatic system and returned back to the blood flow through the chain of lymph nodes, as naturally occurs with plasma proteins.

Circulating macromolecules and colloidal particles are typically taken up by phagocytosing cells, mainly in the liver, spleen and bone marrow. This process is often mediated by opsonization (i.e., a coupling of a polymer molecule or particle to plasma proteins). Many soluble polymers and colloids are rapidly (i.e, within few minutes) removed from circulation by these organs. It is notable that the same polymers and colloids, after local interstitial administration, accumulate in the lymph nodes as a result of their uptake by phagocytosis. The process is similar to uptake by macrophages of the liver, spleen and other organs. Most likely, fast blood clearance caused by phagocytosis in the liver, spleen and other organs does not allow these polymers and particles sufficient time to reach the interstitial space after intravascular injection. In contrast, polymers (e.g., dextran) that pass through lymph nodes after local or intravascular administration without accumulating often circulate in blood for a long time without significant uptake in the liver, spleen and lymph nodes.

Lymphatic tissue consists of well-defined structural components including the cortex (e.g., mainly B-lymphocyte populated areas, including folliculus), the paracortex (e.g., mainly T-lymphocyte populated areas), and the lymphatic sinuses which are often surrounded by macrophage-populated areas. The characteristic structure of a lymph node is altered by diseases, and may be partially or totally replaced by cancer cells in a metastatic process. Therefore, diagnostic agents accumulating selectively in one of the above components are useful for studying both lymph node structure and function, since function influences the efficacy of accumulation.

Delivery of Agents to the Lymphatic Tissues via Intravascular Administration

A system of agent delivery based on diagnostic biologically active or therapeutic substance should: (1) maximize the amount of agent reaching the target area; (2) minimize the concentration of agent in non-target areas; and (3) allow the agent to be retained or released in the target area in active form for a time sufficient for effective action of the agent. The diagnostic and biologically active or therapeutic substances preferably should not cause complications and adverse effects and should be biocompatible, essentially biodegradable.

Diagnostic and biologically active or therapeutic substances of the invention provide effective delivery of an agent to the lymphatic tissue via intravascular administration.

The diagnostic and biologically active or therapeutic substances of the invention are based on the use of soluble polymeric or colloidal complexes and composites exhibiting biological properties which make them suitable for delivering diagnostic and biologically active or therapeutic agents to lymphatic tissues. The agent-carrier complexes accumulate (after intravascular administration) in the lymphatic tissues, and thus deliver diagnostic and biologically active or biologically active, e.g., therapeutic, agents to the site of accumulation, particularly to the lymph nodes.

Macromolecular and colloidal agent complexes of this invention form a family of preparations that have common structural components. The common components of an agent complex are carriers, including outer carbohydrates, and agents. The carriers may be polymeric or particulate. The agents may be diagnostic or biologically active, e.g. therapeutic, and are linked to the inner core of the carrier.

Carriers

Carriers of the invention consist of an inner core, which provides a structure for transporting an agent in vivo, and targeting sites. Target sites include or other moieties capable of binding C3 or a naturally occurring fragment or variant of C3, to allow for the transport of the complex in vivo to a desired location.

Preferably, carbohydrate molecules sterically protect the core and agent against interaction with outside molecules and thus minimize recognition of the core and agent by plasma proteins and cells. The carbohydrate molecules form a diffuse structure and thus allow access of small molecules to the inner part of the complex. The diffuse carbohydrate layer may be replaced by, or combined with, a dense layer not permeable to even small molecules.

Figure 1A:
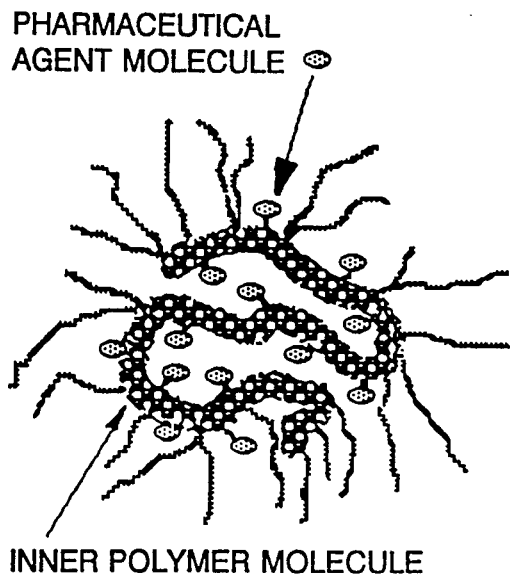
FIG. 1 is a diagram of two schemes of preferred carbohydrate-grafted carriers structures.
Figure 1B:
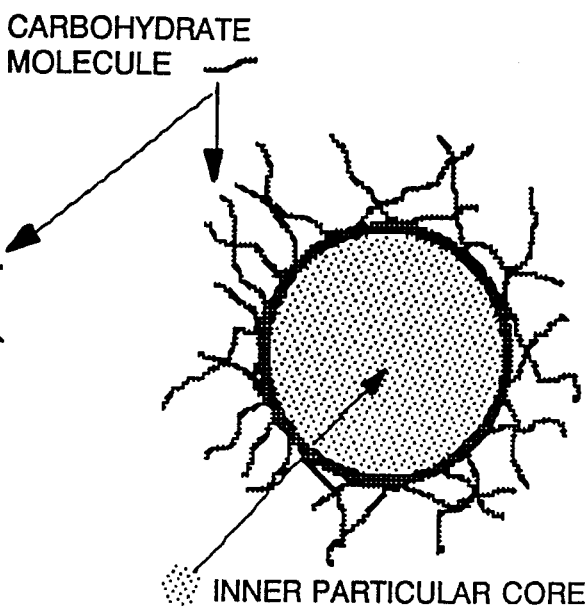
Figure 2:
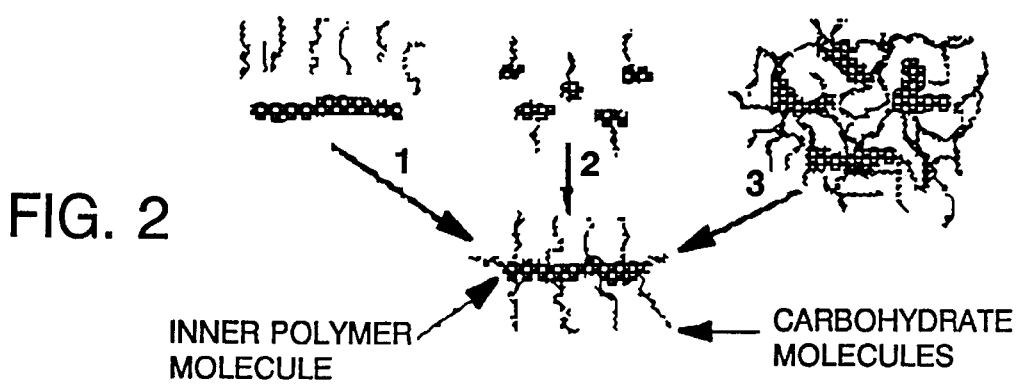
FIG. 2 is a diagram of three basic methods for preparing polymer-based carbohydrate-grafted carriers.

The inner part of the carrier includes a structure of molecules or colloidal particle(s) designed to carry diagnostic and biologically active or therapeutic agents. Due to steric protection provided by the carbohydrate molecules, the contents and structure of the core do not affect distribution of a drug complex in vivo. Hence, any core capable of incorporating an agent may be used in the diagnostic and biologically active or therapeutic substances of this invention if a carbohydrate can be linked, e.g., grafted, to the core thus forming a targeting site and if the total size of the carbohydrate-grafted core does not exceed the limits discussed below. Polymeric molecules and colloidal particles represent preferable core structures of this invention (See FIGS. 1a and 1b). FIG. 1a depicts a polymer-based soluble complex (i.e., the core is a polymer molecule). FIG. 1b depicts a colloidal complex (i.e., the core is a particle). In both, carbohydrate molecules sterically protect the complex.

The carriers of the invention are designed to pass from the vascular space into the lymph nodes. Since the size of a complex may be critical for transfer processes, the total diameter of a carrier should be less than or equal to 100 nm. The test for determining carrier suitability can be performed by filtration of carrier-containing media through a filter with a pore diameter of 0.1 μm. The preferable diameter, e.g., hydrated diameter, of carriers is 10–30 nm, as measured by laser light scattering, gel chromatography or ultrafiltration (dialysis). As the diagnostic and biologically active or therapeutic agents of the invention should not significantly increase the diameter of the carriers of the invention, the total diameter of the diagnostic and therapeutic substances should be less than about 100 nm. Preferably, the diameter, e.g. hydrated diameter, should be in the range of 10–30 nm.

The agent release rates of carriers (e.g., liposomes and polymers) were previously studied to identify preferable carriers of the invention. The structure of a carrier may include additional functional groups for agent coupling and/or release, such as chelates (e.g., diethylenetriaminepentaacetic acid (DTPA)), spacer groups and degradable (e.g., hydrolyzable, oxidizable or reducible) bonds.

Polymeric (Soluble) Carriers

Polymers are often used as agent carriers because of their large capacity for holding agents and their ability to hold many classes of agents. A number of polymers are biodegradable and products of their biodegradation and metabolism are shown to have little or no toxicity. Polymers featuring functional groups that allow carbohydrate linking and agent, e.g. amino group, carboxylic group, and carbonyl group, incorporation are preferable as core components of this invention (e.g., polymers with degradable in vivo chemical bonds (e.g. peptide bonds, hemiacetal or acetate bonds, and ester bonds in the main chain of polymer)). Suitable polymers include polypeptides, polysaccharides, polyesters, and polyamides.

Poly-1-lysine, for example, is a particularly preferred polymer suitable for core formation (See Examples 1–8). The inner cores of poly-1-lysine-based polymeric carriers include a single polylysine molecule, branched poly-1-lysine, or a molecular "skeleton" (See Examples 9 and 10) formed by inner dextran molecules and polylysine molecules, where the dextran molecules were used as a structural component of the core and not as a part of the outer targeting site. These model cores can be modified, e.g., as described in examples 3–8, and loaded with diagnostic and biologically active or therapeutic agents as well.

Particle-based (Colloidal) Carriers

In particle-based carriers, the colloidal particles are preferably grafted by a dense layer of carbohydrate (e.g., dextran) that sterically protects the surface of the colloidal particles against interaction with cells and plasma proteins.

Particle-based carriers are included as a group of preferable carriers of this invention for two reasons. First, certain colloidal particles are known to be effective diagnostic (e.g., superparamagnetic NMR contrast agents) and therapeutic agents (e.g., ferromagnetic agents for local hyperthermia). Second, lipophilic agents could be easily transported in colloidal lipophilic particle cores.

There is no clearly defined difference between formal definitions of polymeric and colloidal materials. Cross-linked polymeric constructions may be classified as colloids or complex polymer molecules.

To demonstrate the feasibility of colloidal particles as a core for diagnostic and biologically active or therapeutic substances of this invention, particle-based carriers with inorganic cores were prepared (See Examples 11–14). The inner core of particle-based carriers consisted of metal hydroxide or oxide particles (e.g., indium hydroxide, paramagnetic iron(III) oxide, and superparamagnetic iron oxide). Paramagnetic iron(III) oxide and superparamagnetic iron oxide can be used as carriers for radionuclide (e.g., $^{111}$In).

Carbohydrates

Carbohydrates, as well as their derivatives and analogues, including fully synthetic polymers, may be divided into four groups, corresponding to their recognition by plasma proteins and cellular receptors.

Group (1) consists of substances directly and specifically recognizable by cellular receptors, such as compounds containing residues of galactose, N-acetylglucosamine and other ligands of specialized cellular receptors.

Group (2) is represented by antigenic compounds that are specifically bound by immunoglobulins present in blood. Ligands of plasma lectins, such as those of mannose binding proteins (MBP), are also bound specifically and hence belong to Group (2).

Group (3) consists of carbohydrates non-specifically recognized only by the complement 3 (C3) component, which binds covalent compounds containing an OH-group or other nucleophilic group able to react with the thioester site of C3. Carbohydrates of other groups are recognized by C3 as well, but other types of interactions prevail over their biological behavior.

Group (4) includes carbohydrates binding to many plasma proteins and cell surface proteins through non-specific interactions (e.g., multiple hydrogen bonds, electrostatic, van-der-Waals and hydrophobic interactions). Since properties of cell surface and plasma proteins are not completely established yet (as evidenced by the recent discovery of the identity of MBP to the light component of Ra-Recognizing Factor) some members of Group 4 may actually belong to Groups 1 or 2. The existence of carbohydrates that are not recognizable in vivo by any mechanism has not been proved.

Carbohydrates have been used as components of agent carriers, although usually not as transporting molecules. Carbohydrates of Group 1, containing receptor-recognizable substances, were studied as transporting components of receptor-targeted agents. Intravascular administration of any member of Group 2 usually results in accumulation of the preparation in the liver and spleen and triggers immediate immunological response. For these reasons they are used mainly as components of vaccines and their use as an intravascular transporting material is not preferable. Carbohydrates of Group 4, in view of their diversity, may not possess common biological properties. It is obvious, however, that the use of Group 4 substances with noncharacterized biological properties is not desirable. Polysaccharides of Group 3 have long-circulating times in blood and are known to be neutral in relation to the receptor systems (e.g., dextran). Polysaccharides were used as convenient biocompatible support molecules and effective stabilizers of colloids but not specifically as a transporting material of polymeric or colloidal drug carriers.

Carbohydrates of Group 3 can be used in the invention. Carbohydrates of Groups 1, 2, and 4 are less preferred.

The suitability of a candidate carbohydrate can be evaluated by determining if the carbohydrate can result in preferential targeting of a diagnostic and biologically active or therapeutic substance of the invention to the lymphatic system. For example, the candidate carbohydrate can be integrated into a diagnostic or therapeutic substance prepared by methods analogous to those of Example 2, labeled according to Example 5, and administered to an animal (e.g., a rat) as shown in Example 16. Carbohydrates suitable for use in the invention display accumulation (of diagnostic and biologically active substance) of greater than 5%, and preferably of greater than 10%, of the injected dose per gram of lymph node tissue in at least one lymph node when administered at a dosage of 1 mg/kg body weight in a rat.

The preferable carbohydrates (e.g., dextran) of this invention should not contain receptor-recognizable, blood lectin-recognizable and highly antigenic sites. Also, the carbohydrates should preferably not bind non-specifically to cell walls and plasma proteins other than to the C3 component (the third component of complement). Carbohydrate molecules for targeting sites which are responsible for carbohydrate-grafted carrier accumulation in the lymph nodes, may or may not accumulate by themselves in a significant amount in the lymph nodes after intravascular administration.

While not being bound by theory, it appears that the carbohydrate-grafted (e.g., dextran-grafted) polymers and colloidal particles of this invention avoid fast recognition in liver and bone marrow, but are readily taken up by lymph node phagocytosing cells. This behavior allows an effective transfer process resulting in localization of intravascularly administered preparations in lymph nodes.

The carbohydrate molecules, especially oligo- and polysaccharides and their analogues, are believed to provide steric protection because they prevent the interaction and adherence of large molecules and components of cell surface proteins with the core and agents of this invention. Steric protection of an inner core is most effective when a large number of long polymeric carbohydrate or analogous molecules are grafted to a carrier. However, the length and number of carbohydrate molecules should be restricted in order to keep the total size of a carrier within the optimal range (i.e., less than 100 nm, preferably 10–30 nm in water media). Additionally, the capacity of a carrier (amount of agent per amount of carrier substance) is larger if small carbohydrate molecules are used. In view of these postulates, oligomeric and polymeric carbohydrates, ranging in size from 1 to 20 kD are preferable.

Examples of preferable carbohydrate molecules include dextran and its synthetic analogues; starch and its derivatives; polyglycosylated synthetic and natural polymers. Other carbohydrates, their derivatives, and other C3 binding molecules may also be used as a component of carriers of the invention. Furthermore, two or more different carbohydrates may be attached to the same carrier to improve its biodistribution.

Synthesis of Carriers

In view of the diversity of possible components and structural details of the carriers of this invention, we provide here the general strategy of synthesis of the carriers focusing on the structural components that are critical for the biological properties of the carrier of this invention. The details of the synthesis of certain carriers are presented in the examples.

The preferable strategy for synthesizing polymer-based and particle-based carriers focuses on the requirements that for a certain core, the number and size of linked carbohydrate molecules should be optimized to: (1) allow reliable steric protection of a core, and (2) provide optimal carrier size and sufficient capacity of a carrier in relation to agent molecules.

Additionally, a third requirement for preferred polymer-based carriers of MRI T1 agents is that the carbohydrate layer should allow diffusion of water molecules to the T1 agent location in the carrier.

Therefore, despite that the number and size of carbohydrate molecules relate directly to the degree of steric protection, overloading of a core with carbohydrate may be not be desirable because it restricts the core space available for agent coupling. To overcome this contradiction, branched polymeric cores or latexes can be used instead of linear core molecules.

Synthesis of Polymer-based (Soluble) Carriers

Polymer-based carriers of the invention are preferably prepared by the following three methods: (1) linking, e.g., grafting, carbohydrates to the polymer molecule; (2) copolymerizing carbohydrate-containing soluble products (e.g., monomers); and (3) decomposing solid polymeric composites or gels (See FIG. 3). The three methods may include multiple stages that may lead to similar products.

The examples of this invention are based on random grafting of carbohydrate molecules on a polymeric core, as it is the most convenient method for laboratory-scale synthesis. Carbohydrate molecules may be attached, for example, by one-point modification, using, for example, a terminal group of oligosaccharide for attaching the carbohydrate to the selected functional groups of the core polymer. By using synthetic heterogenous polypeptides (i.e., consisting of more than one amino acid) and one-point modification, desirable structures for pharmaceutical preparations can be obtained.

The examples show that the agent can be attached to the core polymer before or after the attachment of carbohydrate molecules. If the selective reactions are used, the results of reactions may be, practically the same. Otherwise, non-desirable by-products may be formed. For example, attachment of DTPA-cycloanhydride to the carrier core (e.g., poly-1-lysine) after carbohydrate (e.g., dextran) may cause binding of the DTPA to the dextran molecules by the formation of ester bonds.

Conventional techniques of biochemistry, such as binding of the agent to the carrier with specialized spacer molecules (e.g., the attachment of spacer molecules to the core polymer molecule) may be used as well. To improve biodegradability of a carrier, readily degradable chemical bonds can be introduced into the carrier structure. Spacer molecules may also contain degradable bonds thus providing a system of controlled agent release from a carrier.

Synthesis of Particle-based (Colloidal) Carriers

Figure 3:
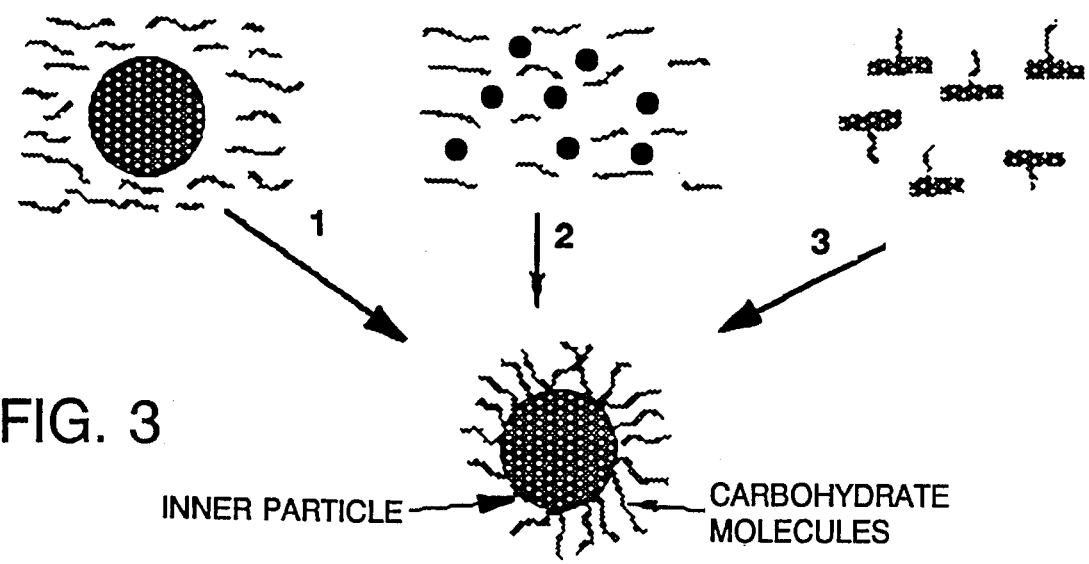
FIG. 3 is a diagram of three basic methods for preparing particle-based carbohydrate-grafted carriers.

Particle-based carriers of this invention are preferably prepared by the following three methods: 1) linking, e.g., grafting, carbohydrates to the microparticle; 2) forming colloidal particles, in the presence of a carbohydrate, (e.g., for inorganic particles); and 3) forming colloidal particles from carbohydrate-containing soluble products (see FIG. 3). The first method is preferable for preparing organic particle-based carriers. The second method is preferable for preparing inorganic particle-based carriers. The third method is preferable for micelle and vessicle formation.

The preferable strategy for synthesizing particle-based carriers focuses on maximizing the number of grafted carbohydrate molecules. In particle-based carriers the quality of steric protection is especially important, because colloidal particles readily adsorb many blood proteins, which cause fast blood clearance and accumulation of particles in the liver and spleen.

While several methods of forming carbohydrate-stabilized (e.g., dextran-stabilized) colloids are known, most of them do not provide reliable protection of particles by their stabilizer. The inventors have found that the success of synthesis depends not only on the method of preparation of particle formation, but also on certain details of reaction conditions. For example, published method of preparing superparamagnetic dextran-coated colloids by precipitating iron oxide in the presence of dextran do not provide significant delivery of these particles to the lymphatic tissues. However, synthesis in the presence of a higher concentration of dextran, a lower concentration of iron salts and under different temperatures (See Example 13) provides formation of densely dextran-grafted particles possessing a biodistribution similar to that of carbohydrate grafted polymers.

Delivery of Carbohydrate-Grafted Carriers to The Lymphatic Tissues

Biokinetics and Biodistribution of Carriers

Biokinetics of carbohydrate-grafted carriers after intravenous administration were studied by γ-scintigraphy through flow studies and multiple static studies in rats and rabbits (See example 15). The circulation parameters were calculated as clearance/accumulation coefficients corresponding to the irreversible capture model described in Papisov, M. et al., "Magnetic Drug Targeting, In Vivo Kinetics of Radiolabelled Magnetic Drug Carriers." Int. J. of Pharm., 1987, 40:201–06, hereby incorporated by reference.

The blood clearance of the preparations was found to be substantially monoexponential within the dose range from 20 μg/kg to 1 mg/kg. The half-clearance time in intact rat at a dose 0.5–1 mg/kg was found to be 2.4 hours for dextran-grafted iron oxide (See example 13), 1.6 hours for dextran-grafted poly-1-lysine (See example 2) and 2.2 hours for dextran-grafted poly-1-lysine-RhX-DTPA (See example 8).

Figure 4A:
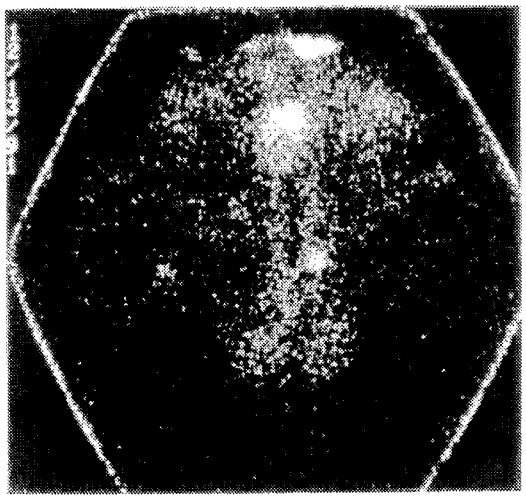
FIGS. 4a–4c are photographs of γ-scintigraphy images in rat and rabbit using a preparation prepared according to Example 2.
Figure 4B:
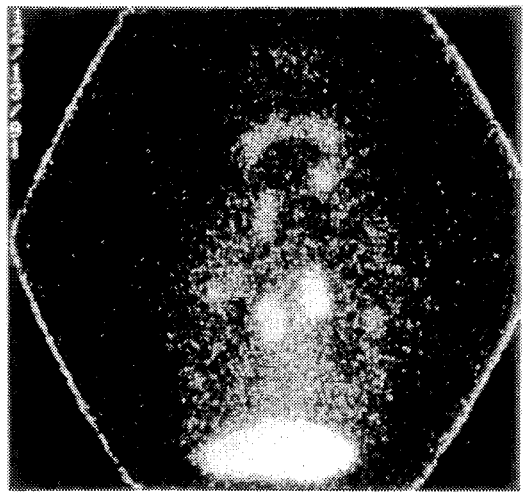
Figure 4C:

Dynamic γ-scintigraphy showed that the mesenteric and paraaortic groups of lymph nodes became recognizable 2–4 hours after injection in rats and 7–10 hours after injection in rabbits. Other nodes developed sufficient signal/background ratios after 6–10 hours in rats and 12–24 hours in rabbits. FIG. 4a (anterior image caudal) shows that the mesenteric and paraaortic groups of the rat lymph nodes displayed remarkable uptake. FIG. 4b (anterior image cranial) shows that the cervical, axillary, and thoracic lymph nodes were visible on the images (the thoracic) in about 50% of rats. FIGS. 4b and 4c (right anterior oblique, rabbit head) show that cervical lymph nodes were less expressed but visible in rats and rabbits. Other lymph nodes displayed variable uptakes, however a majority of them were visualized by γ-images. Spleen activity was high in all cases and the liver showed a much lower concentration of the radioactive label. The liver, spleen and lymph node images show similar signs of activity despite that the ratio of their masses is about 500:40:1. The uptake in other tissues was considered to be substantially comparable to the background in rats and in rabbits. The images did not change significantly during at least 96–100 hours suggesting a low rate of redistribution.

Figure 5A:
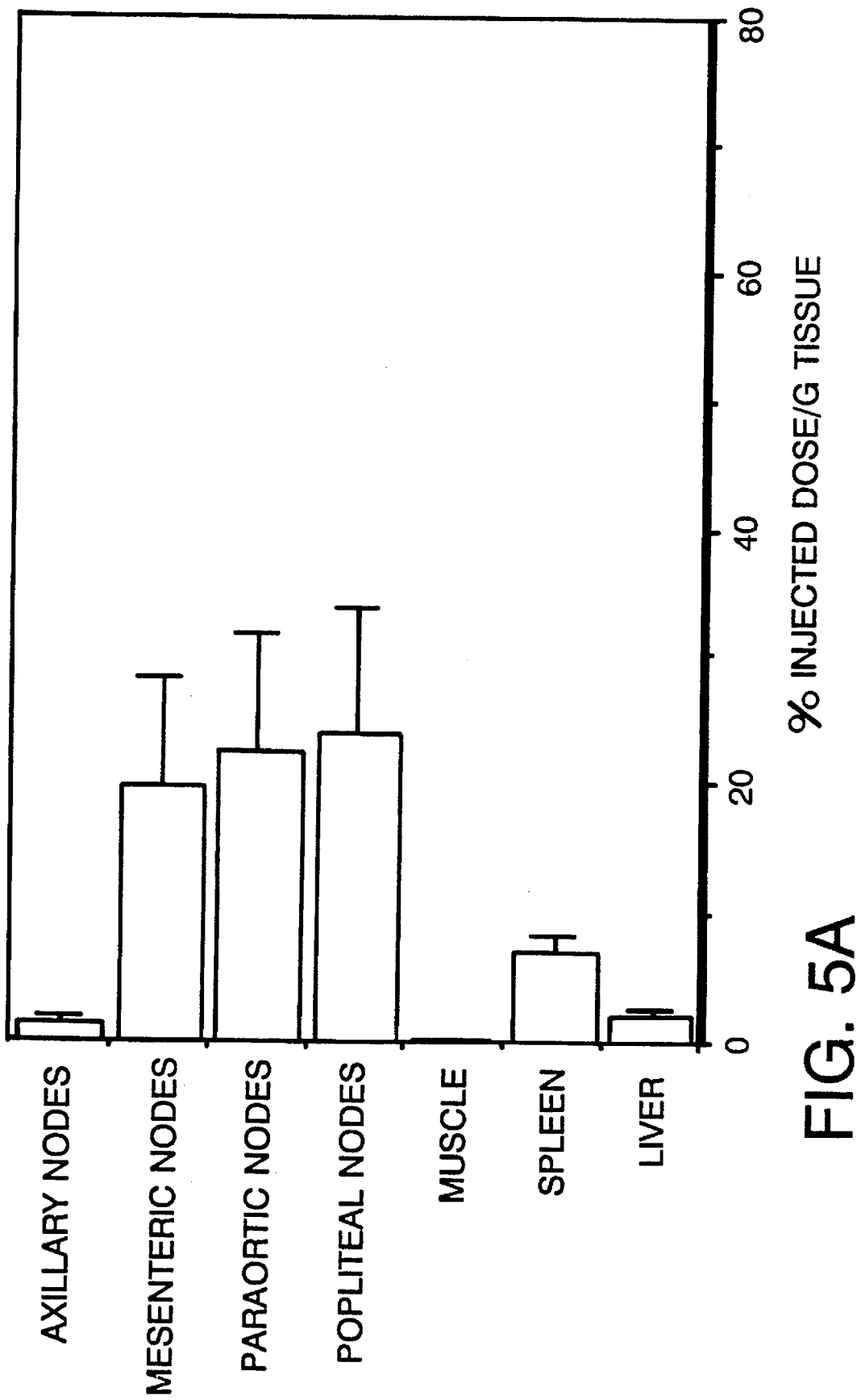
FIGS. 5a and 5b are graphs of 24 hour biodistributions of a radioactively labelled preparations prepared according to Examples 8 (polymer) and 13 (particle)
Figure 5B:
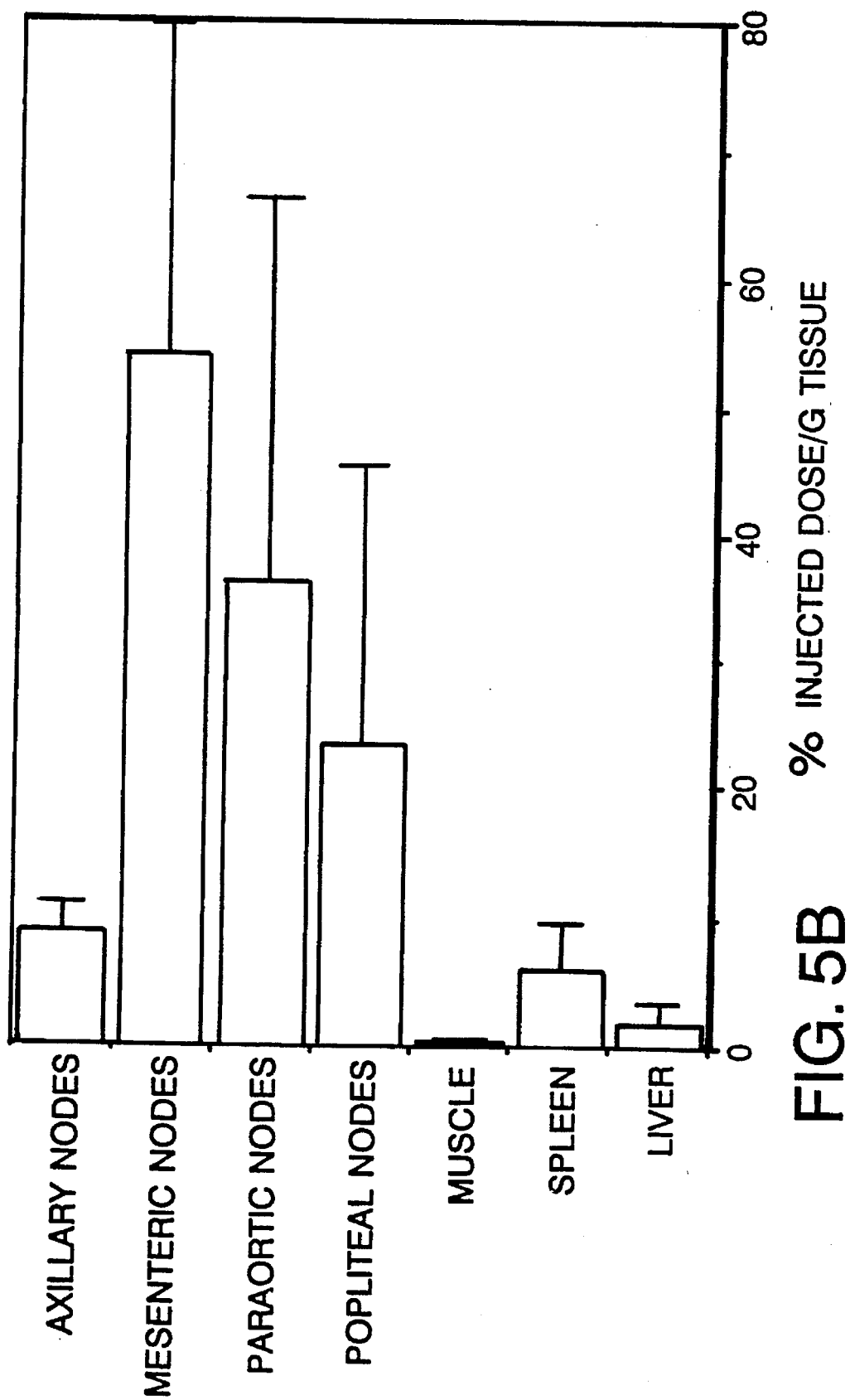

In another experiment (See Example 16) using preparations prepared according to Examples 8 and 13, the biodistribution of a radioactive label was studied in rats following conventional methods (See FIGS. 5a and 5b). The highest uptake of the carriers was found in the mesenteric and paraaortic groups of the lymph nodes (average 20–50% dose per g tissue for different preparations, and up to 140% dose/g tissue in selected cases). Other lymph nodes showed variable uptake. Accumulation of the carriers in other tissues was insignificant (0.01–0.2% dose/g tissue). Experiments following Example 16, but with different doses injected have shown dose dependence of the biodistribution. The optimal range was found to be from 5 micrograms to 50 milligrams of a carrier per kilogram of body weight.

Figure 6:
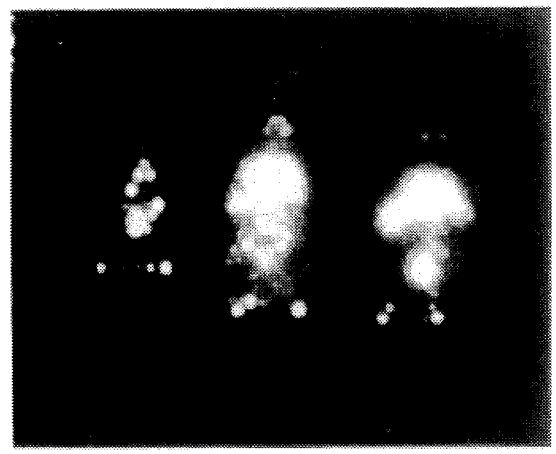
FIG. 6 is a photograph of comparative γ-images of rats 24 hours after local (left image) and intravenous (center and right images) injection of the preparation prepared according to Example 5.

In these studies, we observed transfer of a significant fraction (20% and more) of intravenously administered polymer in the lymph nodes, resulting in accumulation of more than 100% of injected dose per g tissue in some lymph nodes. Local injection of the carbohydrate-grafted preparations also provided effective delivery to the lymph nodes (See FIG. 6). In FIG. 6, the left image resulted from a locally injected carbohydrate-grafted preparation of this invention (See Example 2) and the center and right images resulted from an intravenously injected carbohydrate-grafted preparations of this invention. Local injection of sterically protected carrier preparations demonstrated almost 90% uptake of the material in regional lymph nodes.

Microdistribution Of Carriers in the Lymph Nodes

The microdistribution of the preparations within lymph nodes was investigated by means of optical fluorescent microscopy and autoradiography of lymph nodes harvested 24 hours after intravenous injection of Fluorescein- and In-labelled carriers prepared according to Example 7 (See Example 17). A similar experiment substituting Rhodamine for Fluorescein provided similar results.

Figure 7:
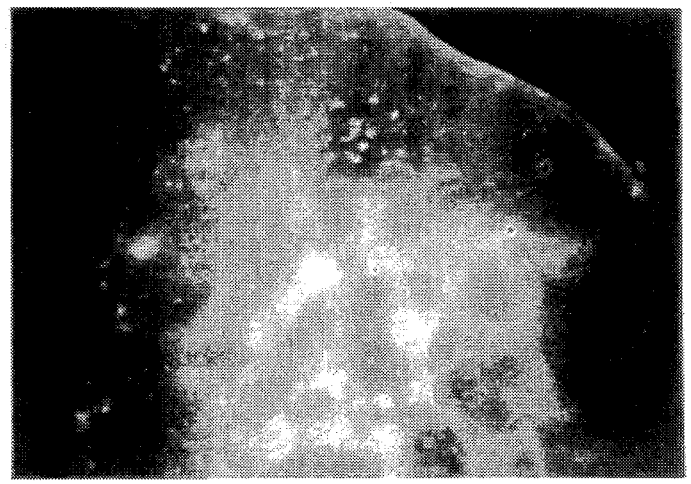
FIG. 7 is a photograph (magnification 80×) of microdistribution of a fluorescent preparation in the lymph node tissue prepared according to Example 7.

Fluorescent microscopy and autoradiography of lymph node tissues demonstrated, as shown in FIG. 7, that the most pronounced accumulation of dextran-grafted poly-1-lysine was in cells located around the sinuses of the lymph node, and in scattered cells of the cortex and paracortex (e.g., macrophages and/or mast cells). The amount of fluorescent material in the areas occupied by lymphocytes was less significant.

The microdistribution of dextran-grafted iron oxide particles was studied by optical microscopy and autoradiography of lymph node tissues 24 hours after intravenous administration (See Example 13). Microdistribution of particle-based carriers was found to be similar to that of the polymer-based carriers. The data and the similar biodistributions of polymeric and particle-based substances of the experiments reported herein are inconsistent with the postulate that a densely carbohydrate-grafted particle core does not, or does not significantly, interact with proteins, cells and other components of the biological system, and thus does not significantly influence the particle biodistribution. In contrast, as was previously shown, that particles having reversibly attached carbohydrate molecules, which are therefore not sterically protected, are cleared from blood by the liver and spleen with a few minutes. (Papisov et al., 1987, Int. J. Pharm).

In one experiment (See Example 18) disposition of a first preparation, prepared according to Example 13, was compared to that of a second preparation, prepared according to Example 8, administered 37 days after the first preparation. In this experiment, an iron oxide particles preparation was administered 37 days before administering a Rhodamine X-labelled polymeric preparation. The lymph nodes were harvested 24 hours after administering the Rhodamine X-labelled preparation. The tissue slices were studied in transmitted light and fluorescent nodes. FIG. 8a is a photograph of the lymph node tissue showing the disposition of iron oxide particles. FIG. 8b is a fluorescent micro photograph of the same area of lymph node tissue as in FIG. 8a and 8b. The disposition of iron storage as shown in FIG. 8a indicates that dextran-grafted particles prepared according to Example 13 do not degrade in lymph nodes and are not metabolized within 30 days. Also, the iron remained stored in an area mainly away from the area of active accumulation of the Rhodamine X-labelled polymeric preparation. See Example 18 for the details of this experiment.

Use of Diagnostic and Biologically Active or Therapeutic Substances Delivered to the Lymphatic Tissues As demonstrated below, the diagnostic and biologically active or therapeutic substances of this invention can be used for the delivery of a wide variety of diagnostic and therapeutic agents. The value of the diagnostic preparations of this invention is based on their selective accumulation in phagocytosing cells of lymph nodes, which could increase sensitivity and resolution of modern diagnostic methods (e.g., Magnetic Resonance Imaging and γ-Scintigraphy) in relation to lymph node disease (e.g., lymphatic cancer). The lymphatic tissues retain carriers of the invention, for an extended period of time (i.e., for several hours or even for days). Long retention time allows the use of these carriers for therapy of the lymphatic tissues, particularly when using the diagnostic and biologically active or therapeutic substances of this invention releasing an agent in the site of accumulation.

Carbohydrate-grafted carriers, due to their long circulation time and penetration into the interstitial space, may also be effectively used for the immobilization of additional target-specific molecules (e.g., antibodies, etc.) providing drug delivery to other targeted tissue exposed to blood or interstitium.

Agents

The agents of this invention include diagnostic and biologically active or therapeutic agents. Agents are incorporated into the carrier, preferably the carrier core by means of chemical coupling, complex formation, encapsulation or any method providing agent retention within macromolecular or particulate complexes.

The number of agent molecules transported by a single carrier molecule or particle depends only on agent size and varies from one for large molecules to a few hundred for small molecules such as chelating groups.

The upper limit of the size of the agent molecule transported by carriers of this invention depends on the size of the carrier itself, and should not exceed the optimal size for the biodistribution of the pharmaceutical complex. For example, because of their relatively large size only a limited number of protein molecules may form the core structure of this invention and remain within the macromolecular complex optimal diameter limits. Recent developments in the methods of biochemistry make it possible to form a carrier core incorporating almost any protein without a significant loss of specific activity of the protein.

In view of the above, the diversity of agents that can be transported by the carbohydrate-linked carriers suggests a wide variety of applications of the diagnostic or therapeutic substance of this invention. The diagnostic agents include radioactive labels (e.g., indium, technetium, iodine, and gallium) for both γ-scintigraphy and photon emission tomography); magnetic labels, (e.g., T1 and T2 agents for nuclear magnetic resonance imaging based on, e.g., iron, gadolinium, manganese, and dysprosium compounds); and stable isotopes (e.g., phosphorous, silicon, and sodium as NMR spectral labels).

The biologically active and therapeutic agents include e.g., alpha or beta emitting radioactive isotopes; inorganic compounds (e.g., magnetite as an agent for local hyperthermia); and organic compounds (e.g., proteins, peptides, enzymes, toxins, hormones, inhibitors, and antibiotics). Carbohydrate-linked e.g., carbohydrate-grafted, compounds loaded with antineoplastic agent or immunomodulator may be used, as targeted antimetastatic lymphotropic drugs. As shown in Examples 7 and 8, two or more different agents may be connected to the carrier at the same time.

Additional examples of diagnostic and biologically active or therapeutic substances of this invention and their possible applications include those listed in Table 1.

TABLE 1

| Application | Loaded with: | Purpose |
|---|---|---|
| Diagnostic | gamma-emitters Paranagnotic | Lymph nodes scintigraphy |
|  | T1 agents | Lymphatic tissues MR imaging |
|  | T2 agents | Lymphatic tissues MR imaging |
|  | Radiopaque agents | Lymphatic tissues CT scanning |
|  | Ultrasound scattering agents | Lymphatic tissues ultrasonography |
| Therapeutic | Beta or alpha-emitters | LN metastases radiotherapy |
|  | Immunomodulators | Preventive LN metastases treatment |
|  |  | Systemic immunomodulation |
|  |  | Extermination of the infected lymphocytes by activated macrophages |
|  | Anticancer drugs | LN metastases chemotherapy |
|  | Antigens | Immunization |

Carrier Capacity and Biodistribution

The unique pharmacokinetics of carbohydrate-linked polymers that are transferred from blood to lymph nodes allow their use as agent carriers for the development of intravascular lymphotropic diagnostic and therapeutic substances.

Carriers of the invention are characterized by their: (1) potentially large capacity, because the inner core (e.g. polylysine) may be loaded with a large amount of diagnostic label or biologically active compound, and (2) the capability to hold and transport diverse agents. The examples of this invention show that a wide range of the agents (e.g., radionuclides, T1 (gadolinium) and T2 (superparamagnetic iron oxide)); NMR contrast agents; and organic molecules (DTPA, Rhodamine X)) can be connected to or used as the inner core of a carrier (See Examples 5, 6, 7, 8, 13).

In the site of accumulation, agent behavior depends on the method of its attachment to a carrier. The agent-to-carrier bond therefore should be chosen to provide effective agent action. The majority of diagnostic agents (e.g., radionuclides and NMR and X-ray contrast agents), and some therapeutic agents (e.g., enzymes) may fulfill their purpose while linked to the carrier. Most biologically active or therapeutic agents, however, should be released from the carrier so they can function in a free, unbound form. Therefore, the chemical structure of a carrier can be considered optimal if it allows the use of different chemical bonds between the agent and carrier without a loss of the properties of the carrier. Examples 2 and 4 show that a diversity of functional groups and spacer molecules can be incorporated in a polymeric core.

The biodistribution of a carbohydrate-grafted carrier of this invention with a grafted agent is expected to be similar to that of a carbohydrate-grafted carrier without an agent. To estimate the influence of an agent on the biodistribution of carrier, Rhodamine X (RhX; Molecular weight=584 D) was chosen as an organic molecule agent. A large amount of RhX molecules were immobilized on the polylysine core of the carrier (Example 8) to simulate the structure of a therapeutic macromolecular complex. The biodistribution of this preparation was studied by γ scintigraphy and by conventional methods and has been shown to be similar to the biodistribution of RhX-free carrier. Table 2 and FIGS. 9a and 9b present examples of biodistribution.

TABLE 2

Typical example of biodistribution of dextran-linked polylysine loaded with Rhodamine X

| Tissue | Complex accumulation, % dose/g tissue |
|---|---|
| Lymph nodes: | |
| paraaortic | 113.40 |
| mesenteric | 34.10 |
| thoracic | 19.30 |
| popliteal | 41.30 |
| cervical | 2.00 |
| Spleen | 20.30 |
| Liver | 1.50 |
| Muscle | 0.02 |

Behavior of carbohydrate-grafted Carriers in Experimental Pathology Models

The accumulation of the carbohydrate-grafted preparations in the lymph node depends on the state of the surrounding tissue. In an experiment (See Example 19) using a preparation prepared according to Example 7, the effect of inflammation on uptake was studied. Acute inflammation was found to cause increased uptake of the preparation in the nearest regional lymph node (See FIG. 10a). It was shown in this experiment that the preparation accumulates in the area of the inflammation as well. Analogous results were obtained in an experiment on rats with growing cancer in the right front extremity (See Example 20 and FIG. 10a). In this experiment, hyperplasia was found by histological methods in the node draining cancer area. This may explain the increased accumulation of the preparation in the lymph node.

The mechanism of carrier accumulation in the inflammation site is probably similar to that in a lymph node. Using fluorescent microscopy and autoradiography, accumulation in the cancer site was attributed mainly to the uptake in the scattered cells (e.g., recruited macrophages) rather than in the cancer tissue. Increased vascular permeability in the inflammational site may also contribute to accumulation. The amount of preparation accumulated per gram of cancer tissue was much less than the amount accumulated per gram of normal and hyperplastic lymph node tissue. Therefore, the invention is expected to be useful, particularly, for the diagnosis, prevention and treatment of lymphatic metastases and for differentiation of metastases and lymph node hyperplasia.

EXAMPLES

Example 1: Synthesis of dextran-grafted poly-1-lysine

Dissolve 2 g of dextran (MW 10 kD) in 5 ml of water and dissolve 0.4 g of sodium periodate in 1.5 ml of water. Mix the dextran and sodium periodate solutions and incubate for one hour at room temperature or for 12 hours at 4° C. under stirring. Then dilute the reaction mixture with water to 200 ml. Concentrate the solution to 5 ml using ultrafiltration Amicon cell equipped with YM3 membrane. Repeat the dilution and concentration steps to remove low-molecular weight products of the reaction. Then dissolve 20 mg of poly-1-lysine (MW 70 kD) in 2 ml of sodium citrate buffer solution (0.1M, pH 8.3). Mix the concentrated solution of oxidized dextran and the poly-1-lysine solution under intensive stirring. Incubate 20 minutes under stirring. Dissolve 20 mg of sodium cyanoborohydride in 1 ml of water and add to the reaction mixture. Stir the reaction mixture for 24 hours at room temperature. Dilute the reaction mixture to 200 ml with water, than concentrate the solution to 5 ml using ultrafiltration Amicon cell equipped with YM100 membrane. Perform dilution and concentration steps a total of three times each. Then lyophilize the product, or add 0.1 ml of 0.1M sodium citrate and store in the solution.

The dextran-grafted poly-1-lysine may be modified by the attachment of a chelating or other group to the inner polymer (poly-1-lysine) aminogroups as in Examples 2–4.

Example 2: Synthesis of dextran-grafted diethylenetriaminepentaacetic acid [DTPA] modified poly-1-lysine Dissolve 1 mg of dextran-grafted poly-1-lysine from Example 1 in 0.1 ml of 0.1M sodium borate solution and cool the solution in an ice bath. Dissolve 5 mg of DTPA-cycloanhydride in 0.1 ml of dimethylsulfoxide (DMSO). Add the DTPA-cycloanhydride solution to the dextran-grafted poly-1-lysine solution at 4° C. and stir intensively. Then incubate 12 hours at 4° C. Separate the product using gel-chromatography column, 10×1 cm or similar, filled with Sephadex G-100 or analogous gel, and 0.9% NaCl as an eluant. Lyophilize the product or store in the solution.

Example 3: Synthesis of dextran-grafted [N-hydroxysuccinimido-bis-dithiopropionyl]poly-1-lysine Dissolve 1 mg of dextran-grafted poly-1-lysine from Example 1 and 0.01 ml of triethylamine in 0.1 ml of DMSO. Dissolve 5 mg of (dithio-bis-dipropionyl)-di-N-hydroxysuccinimide in 0.1 ml of DMSO. Add the (dithio-bis-dipropionyl)-di-N-hydroxysuccinimide solution to the dextran-grafted poly-1-lysine solution and stir intensively. Then incubate 1 hour at 20° C. Separate the product using a gel-chromatography column, 10×1 cm or similar, filled with Sephadex G-25 or analogous gel, and DMSO as an eluant. Lyophilize the product or store in the frozen solution at −20° C.

This carrier may be used for the direct coupling of the amino-compounds.

Example 4: Synthesis of dextran-grafted [3-mercaptopropionyl]poly-1-lysine

Dissolve 1 mg of dextran-grafted [N-hydroxysuccinimido-(bis-dithiopropionyl)]poly-1-lysine from Example 3 in 0.1 ml of 0.1M sodium citrate solution. Incubate for 1 hour at 37° C. Add 10 µl of dithioerithritol and stir. Then incubate 1 hour at 37° C. Separate the product using a gel-chromatography column, 10×1 cm or similar, filled with Sephadex G-100 or analogous gel, and 0.9% NaCl as an eluant. Store under nitrogen, at −20° C.

This carrier may be used for the direct coupling of the SH-group containing compounds and for the transportation of metal ions possessing high affinity to the sulfide group.

Examples 5–9 are labeled polymeric carriers with radionuclide and T1 magnetic resonance contrast agents. Because of the incompatibility of the optimal pH range for DTPA chelating and the optimal pH range for stability of the hydrated ion ($In^{3+}$ and $Gd^{3+}$), labeling is performed by ligand exchange.

Example 5: poly-1-Lysine[$^{111}$In-DTPA], dextran-grafted

Mix a solution of $^{111}$InCl$_3$ in 0.04M HCl, mCi, with 5-fold volume of 0.1M sodium citrate buffer solution, pH=5.3–5.5 (or use a commercially available indium-111 citrate solution). Dissolve 100 µg of poly-1-lysine[DTPA]dextran, as in Example 2, in 0.1 ml of 0.1M sodium citrate buffer solution, pH=5.3–5.5.Mix the solutions and incubate at room temperature for 30 minutes. After incubation, if necessary, add 1 mg of CaCl$_2$ to deactivate the remaining DTPA groups. Replace the media to 0.9% NaCl by means of gel-chromatography (Sephadex G-25, 0.5% NaCl as an eluant).

Example 6: Poly-1-Lysine[Gd-DTPA], dextran-grafted

Prepare a solution of GdCl$_3$.6H$_2$O, 10 mg/ml, in 0.2M sodium citrate buffer solution, pH=5.3–5.5. Dissolve 10 mg of poly-1-lysine[DTPA]dextran as in Example 2, in 0.1 ml of water. Mix 2 ml of the GdCl$_3$ sodium citrate and the poly-1-lysine solutions and incubate at room temperature for 30 minutes. Replace the media to 0.9% NaCl by means of gel-chromatography (Sephadex G-25, 0.9% NaCl as an eluant).

Example 7: Poly-1-lysine[Gd,$^{111}$In-DTPA][Fluorescein]dextran-grafted

Prepare poly-1-lysine-dextran, as in Example 1, and add 1 mg in 1 ml of 0.1M sodium borate, pH=9.3. Prepare a solution of 0.2 mg of Fluorescein isothiocyanate in 100 µl of DMSO. Inject the Fluorescein isothiocyanate solution into the poly-1-lysine dextran solution under intensive stirring. Incubate at room temperature for 30 minutes. Dissolve 5 mg of DTPA-cycloanhydride in 0.1 ml of DMSO. Add the DTPA-cycloanhydride solution to the poly-1-lysine[Fluorescein]-dextran solution and stir intensively. Then incubate 12 hours at 4° C. Separate the product using a gel-chromatography column, 10×1 cm or similar, filled with Sephadex G-100 or analogous gel, and 0.9% NaCl as an eluant. Mix a solution of $^{111}$nCl$_3$ in 0.04M HCl, 1 mCi, with a 5-fold volume of 0.1M sodium citrate buffer solution, pH=5.3–5.5 (or use commercial indium-111 citrate solution). Mix the poly-1-lysine[DTPA-Fluorescein]-dextran and the $^{111}$InCl$_3$-HCl-sodium citrate solutions and incubate at room temperature for 30 minutes. Prepare a solution of GdCl$_3$.6H$_2$O, 10 mg/ml, in 0.2M sodium citrate buffer solution, pH=5.3–5.5. Add 0.2 ml of the GdCl$_3$-sodium citrate to the reaction mixture and incubate at room temperature for 60 minutes. Separate the product by means of gel-chromatography (Sephadex G-25, 0.9% NaCl as an eluant).

Example 8: Synthesis of dextran-grafted Poly-1-lysine loaded by Rhodamine X (RhX) and labelled with chelating group (DTPA)

Dissolve poly-1-lysine hydrobromide, 10 mg, (MW 40 kD, Sigma) in 1 ml 0.1M sodium borate (pH=9,3). Dissolve DTPA cycloanhydride (Pierce), 4 mg, in 50 μl DMSO and add to cold (5° C.) Poly-1-lysine solution under stirring. Dissolve rhodamine X isothiocyanate (Molecular Probes), 3.0 mg, in 20 μl DMSO and add to reaction mixture. Incubate the resultant solution for 2 hours at room temperature. Purify the product, Poly-1-lysine(RhX)(DTPA), by gel-chromatography on Sephadex G-25 (Pharmacia).

Dissolve dextran, 1 g (MW 10 kD, Pharmacia) in 5 ml H$_2$O and mix with 2 ml NaIO$_4$ solution, 100 mg/ml H$_2$O. After 1 hour incubation, dilute the reaction mixture to 100 ml with water and then concentrate to 5 ml using Amicon YM3 membrane to remove salts. Perform the dilution and concentration steps a total of three times each.

Mix the solution of oxidized dextran with the Poly-1-lysine[RhX][DTPA]solution and then with 50 ml of Sodium Cyanoborohydride solution (1 mg/ml) in 0.1M tri-sodium citrate (pH=8.3). Stir the reaction mixture for 24 hours at room temperature. Separate the dextran-grafted polymer using Amicon XM50 membrane, purify by gel-chromatography (Sephadex G-100) and liophylize.

The synthetic technique described above was developed to obtain the polymer composition Poly-1-lysine[RhX][DTPA] randomly grafted by dextran. The product contained 24 molecules of dextran per polylysine molecule (average, assuming MW=40 kD for PL and 10 kD for dextran), 4% of Rhodamine X (w/w); capacity for metal ions: 0.15 μm/mg.

Example 9: BranChed poly-1-lysine core polymer

Dissolve 100 mg of poly(ε-N-carbobenzoxy (CBZ)) lysine, MW=10 kD, in 2 ml DMSO. Add 0.1 mg of sodium nitrite and stir. Add 2 mg of dicyclohexylcarbodiimide, stir and incubate for 10 minutes. Dissolve 10 mg of poly-1-lysine, MW=10 kD, in 100 μl of DMSO and add to the reaction mixture. Incubate 24 hours under stirring. Remove the precipitate by centrifugation. Liophylize the product. Add 5 ml of HBr/Acetic acid reagent and stir. Incubate for 1 hour in a sealed tube. Separate the precipitate and wash with dry ether, 5 ml, not less than 5 times.

Branched poly-1-lysine hydrobromide can be used as a core polymer in the syntheses analogous to those of Examples 1–8.

Example 10: Dextran-Poly-1-lysine molecular "skeleton"

Dissolve 1 mg of dextran, MW=10 kD, in 0.2 ml of water. Dissolve 0.5 mg of potassium periodate in 0.1 ml of water and mix the solutions. Stir and incubate for 1 hour at room temperature. Prepare a solution of 20 mg poly-1-lysine, MW=10 kD, in 1 ml of 0.1M sodium borate, pH=9.3. Mix the solutions of oxidized dextran and poly-1-lysine. Incubate for 20 minutes under stirring. Prepare solution of 3 mg of sodium cyanoborohydride in 0.5 ml of water and add to the reaction mixture. Stir and incubate for 12 hours. Purify the product by gel-chromatography (Sephadex G-100) and liophylize.

Poly-1-lysine-dextran conjugate may be used as a core "skeleton" polymer in the syntheses analogous to those of Examples 1–8.

Example 11: Iron (III) oxide β-glucan grafted particle, In labeled (microsynthesis)

Dissolve 2 mg of yeast β-glucan in 5 μl of water. Dissolve 2 mg of FeCl$_3$.6H2O in 10 μl of water. Mix the β-glucan solution and 1 μl of the FeCl$_3$.6H2O solution in a small (1 ml) polypropylene centrifuge tube equipped with stopper. Add 1 ml of $^{111}$InCl$_3$ solution. Put a small piece of a chromatographic paper dampened by saturated NH$_3$ solution into the upper part of this tube (NH$_3$ solution should not be dropped into the reaction mixture and the paper should not contact the solution. The NH$_3$ is to be transferred to the reaction mixture through the gas phase). Close the tube and place into a 70° C. water bath for 30 minutes. Separate the product using a gel-chromatography column, 10×1 cm or similar, filled with Sephadex G-100 or analogous gel, and 0.9% NaCl as an eluant.

Example 12: Indium hydroxide-β-glucan[fluorescein]

Inject under very intensive stirring 50 μl of $^{111}$InCl$_3$ solution in 0.04M HCl into 0.5 ml of yeast β-glucan-fluorescein solution, 0.5 mg/ml, and then add 5 ml of 30% ammonia. Incubate the product at 70° C. for 30 minutes. Separate the product using gel-chromatography (Sephadex G100 and 0.9% NaCl as an eluant).

Example 13: Superparamagnetic iron Oxide particle densely grafted by dextran

Dissolve 1.55 g of dextran (MW 10 kD) in 3 ml of water. Stir the solution for 30 minutes at room temperature. Dissolve 0.105 g of FeCl$_3$.6H20 and 0.039 g of FeCl$_2$.4H20 in the solution of dextran and cool the resulting solution to 4° C. Slowly add a 30% ammonia solution dropwise under very intensive stirring until the pH of the solution is increased to 10.5. Then incubate the product at 70° C. for 45 minutes under stirring and separate the product using ultrafiltration (membrane YM300) or gel-chromatography (Sepharose CL2B or Sephacryl S300).

Example 14: Iron oxide Ficoll-grafted particle

Dissolve 20 g of Ficoll (the trade name for a synthetic polymer of sucrose; MW 40 kD) in 20 ml of water and stir the solution for 30 minutes at room temperature. Dissolve 0.1 g of $FeCl_3.6H_2O$ in a solution of Ficoll and cool the resulting solution to 4° C. Slowly add a 30% ammonia solution dropwise under very intensive stirring until the pH of the solution is increased to 10–10.5. Incubate the product at 70° C. for 30 minutes under stirring. Separate the product using ultrafiltration (membrane YM300) or gel-chromatography (Sepharose CL2B or Sephacryl S300).

Although the above examples present general and specific guidelines for preparing sterically protected drug carriers according to this invention, one skilled in the art can assemble additional candidate molecules and compare their characteristics to molecules claimed by the invention.

Animal Experiments

Example 15: Gamma-scintigraphy on rats and rabbits

Animal experiments were performed on 22 Sprague Dawley rats (250–300 g) and 4 white New Zealand rabbits (2–2.5 kg). Animals were anesthetized with pentobarbital (rats) or ketamine (rabbits). Radiolabelled polymer, (prepared following Examples 1 and 5), 1 mg/kg, 0.3–1 mCi/kg, was injected into the tail vein. Biokinetics of preparations was studied by dynamic γ-scintigraphy. Static images were acquired 24 hours after injection. Results are presented in FIGS. 4a–4c.

Example 16. Biodistribution of polymeric and colloidal dextran-grafted preparations Animal experiments were performed on 16 Sprague Dawley rats (250–300 g). Animals were anesthetized with pentobartibal. Radiolabelled polymer (prepared following Example 8) or particles (prepared following Example 13), 1 mg/kg, 0.1–1 mCi/kg, were injected into the tail vein. Accuracy of injections was controlled by γ-scintigraphy. Animals with activity registered in the tail tissue were excluded from the experiment. Animals were sacrificed and tissues were extracted for biodistribution studies 24 hours after injection. Results are presented in FIGS. 5a (polymer-based and 5b (particle-based).

Example 17: Microdistribution of fluorescent, radionuclide-labelled preparation in the lymph node tissue Animal experiments were performed on 6 Sprague Dawley rats (250–300 g). Animals were anesthetized with pentobarbital. Radiolabelled fluorescent polymer (prepared following Example 7) 1 mg/kg, 0.1 mCi/kg, was injected into the tail vein. Accuracy of injections and biodistribution were controlled by γ-scintigraphy. Animals were sacrificed and tissues were extracted for microdistribution studies 24 hours after injection. Lymph node tissues were frozen and 5–7 µm slices were prepared without fixation. Fluorescent microscopy was performed using Zeiss Axiovert 35 microscope. Accumulation of fluorescent material was most significant in the cells located in the areas surrounding sinuses (identified as most likely macrophages) and also in the sinus lining cells. Scattered cells of paracortex, cells surrounding follicles and intrafollicular macrophages also accumulated a significant amount of fluorescent material. Typical microdistribution of a preparation is presented in FIG. 7.

EXAMPLE 18. Comparative microdistribution of preparations 24 hours and 37 days after administration Animal experiments were performed on 2 Sprague Dawley rats (350 g). Animals were anesthetized with pentobarbital. Radiolabelled superparamagnetic iron oxide particles, 50 µm of iron per kg, (prepared following Example 13) were administered via tail vein and 24 hours later their biodistribution was controlled by γ-scintigraphy. Radiolabelled fluorescent polymer (prepared following Example 8) 1 mg/kg, 0.1 mCi/kg, was injected via tail vein into the same animals 37 days after the injection of iron oxide particles. Accuracy of injections and biodistribution were controlled by γ-scintigraphy. Animals were sacrificed and tissues were extracted for microdistribution studies 24 hours after injection. Lymph node tissues were frozen and 5–7 µm slices were prepared without fixation. Fluorescent microscopy was performed using Zeiss Axiovert 35 microscope. Accumulation of fluorescent material was found to be analogous to that described in Example 17. Iron deposits (absent in normal rats) were formed in perisinusoidal areas mainly of the medulla and paracortex. The locations of accumulation differed from those of the fluorescent label. Fluorescent (See FIG. 8b) and transmitted-light micrographs (See FIG. 8a) of the same lymph node area after administration of the iron oxide particles and the Rhodamine X-labelled polymeric preparation are presented.

Example 19. Study of carbohydrate-grafted poly-1-lysine distribution in the animals with induced inflammation Animal experiments were performed on 4 white New Zealand rabbits (3–3.2 kg). Acute inflammation was induced, as previously described, in the leg tissue via injection a suspension of staphylococcus aureus suspension having $1 \times 10^9$ bacteria. A preparation prepared according to Example 7 was administered the 3rd day after infection. Animals were anesthetized with ketamine. Radiolabelled polymer, 1 mg/kg, 0.3 mCi/kg, was injected into the ear vein. Static images were acquired 48 hours after injection. Results are presented in FIG. 10a as an anterior image of the caudal area.

Example 20: Study of carbohydratesgrafted poly-1-lysine distribution in the animals with induced mammary adenocarcinoma Animal experiments were performed on 24 Fisher rats (200–250 g). Mammary adenocarcinoma of the front right leg tissue was induced via subcutaneous implantation of $10^7$–$10^8$ R3230AC cells (obtained from Biomeasure, Hopkinton, Mass.). A preparation prepared according to Example 7 was administered at the 10th day after implantation. Animals were anesthetized with pentobarbital. Radiolabelled polymer, 1 mg/kg, 0.3 mCi/kg, was injected into the tail vein. Static images were acquired 24 hours after injection. Results are presented in FIG. 10b as an anterior image of cranial body area.

Example 21: Application of the carbohydrate-grafted carriers for magnetic resonance measurements A carrier prepared according to Example 8 was labelled with $^{111}In$ and loaded with Gadolinium as described in Example 7. The preparation was administered to 5 rats at a concentration of 15 μm of Gd per kg body weight as described in Example 16. Mesenteric lymph nodes were extracted 24 hours after administration and pooled into one sample tube. Relaxation time, T1, of the lymph nodes was measured at 37° C., 0.47 T using inversion recovery pulse sequence. Relaxation time of the mesenteric lymph nodes was found to be decreased to 154 ms compared to 476 ms in the control group of 5 rats.

Use

The substances of the invention are generally administered at dosage less than 2 grams/kilogram of body weight and preferably at a dosage of between 5 micrograms and 50 milligrams/kilogram of body weight.

Other Embodiments

Other embodiments are within the following claims, e.g., the preparations based on the carriers may be produced as convenient pharmaceutical formulations without unusual requirements for storage conditions.

The diagnostic preparations for γ-imaging may be formulated as a non-radioactive kit adjusted for labeling immediately prior to injection. Thus, the polymer prepared following Example 2 of the invention may be used in combination with a citrate buffer composition, in lyophilized form or in solution. If necessary, DTPA groups may be replaced by other chelating groups for labelling with various radionuclides.

Magnetic resonance contrast agents can be prepared in advance and stored either as solid compositions or as solutions. For some indications gadolinium may be substituted by other paramagnetic metal ions with different T1 and T2 relaxivities without significant change of technology.

The targeted biologically active compounds may be prepared using technologies close to those of the above examples and for diagnostic preparations. Optimization of pharmaceutical formulation should depend, most of all, on the storage requirements of the biologically active agent, if the agent used is unstable at certain conditions. Generally, there are no obstacles for the production of the carbohydrate-linked polymers and microparticles in the lyophilized form with stabilizing and pharmacologically desirable (e.g., facilitating dissolution) additives.

Diagnostic and therapeutic substances of the invention can possess one or more of the following qualities: the targeting sites are distributed on the carrier such that when the substance is injected intravascularly into an animal e.g., a rat or rabbit at a dosage of 1 mg per 1 kg body weight of the animal, at least 5% of the injected dose of the substance per gram of lymph node tissue accumulates in a lymph node; the targeting sites are distributed on the substance such that when the substance is exposed to rat blood plasma containing 1 mM sodium citrate for two hours at 37° C., more than 80% of the protein absorbed to the substance is C3 or its naturally occurring variants; the targeting sites are distributed on the substance such that when exposed to rat plasma containing 1 mM sodium citrate for 2 hours at 37° C. the substance absorbs less than 50% of its weight in blood plasma proteins; the said targeting sites are distributed on the substance such that when the substance is exposed to rat plasma containing 1 mM sodium citrate for two hours at 37° C., greater than 80% of the protein absorbed to the substance is C3 or its naturally occurring variants and the substance absorbs less than 50% of its weight in blood plasma proteins; and (in embodiments wherein the carrier or agent include iron); the targeting sites are distributed on the substance such that when the substance is exposed to rat plasma containing 1 mM sodium citrate for 2 hours at 37° C. the substance binds less than 1 molecule of transferring per particle of said substance; 0.01–1.0 mg/ml mixture of the substance in a 0.9% NaCl in water solution will not aggregate or precipitate during the first 24 hours of incubation after the substance is added to the solution when incubated at 25° C.; a 0.01–1.0 mg/ml mixture of the substance in 0.9% NaCl in water solution will not aggregate or precipitate during the first 72 hours of incubation after the substance is added to said solution when incubated at 37° C. in a homogenous magnetic field at 0.47 Tesla.

These properties can be used to determine if a substance is suitable for use in the invention using e.g., the following protocol. Prepare blood plasma of intact normal rat, containing a minimal amount, e.g. 1 mM of sodium citrate to prevent fibrin formation. Incubate the carrier (or substance) in question in said plasma for 2 hrs at 37° C. Separate said carrier or substance from plasma, e.g. by ultracentrifugation. Compare protein binding to the carrier or substance in question with that of carrier of the invention (e.g., prepared according to the examples 2 or 13), e.g. by electrophoresis and immunoblotting. While carriers of the invention bind mainly C3 and its naturally occurring variants and fragments, other carriers, e.g. iron oxide particles, bind significant amounts, e.g. 10–1500% w/w in relation to the bound C3, of transferrin, immunoglobulines or other proteins.

In inorganic, e.g. iron-containing particles, the binding of transferrin may indicate the presence of the exposed unprotected particle surface or presence of non-desirable forms of metal, e.g. iron, compounds in the diagnostic and biologically active or therapeutic substances or carriers. Iron-containing substances and carriers of the invention do not bind more than 1 transferrin molecule per particle under the above conditions.

The binding of immunoglobulines and other proteins may indicate non-specific adsorption of a protein on an unprotected particle surface as well as the presence of non-desirable components in the carrier or substance structure, e.g. in the targeting site, e.g. the presence of carbohydrate molecules altered in the process of substance synthesis. The presence of other proteins may indicate non-specific adsorption or non-specific or specific interaction of a protein with a carrier or a substance of the invention. The binding of transferrin, immunoglobulines and other proteins increase recognition of a carrier in the liver, bone, marrow, spleen and other areas and decrease carrier accumulation in the lymph nodes.

These procedures can also be used to optimize parameters of the substances of their manufacture.

We do not expect any serious problems with toxicity and sterility of this inventions protected preparations. The starting materials used, for example, for the synthesis of our model preparations are essentially biodegradable and they may be obtained in a sterile, apyrogenic form. In addition, the final preparations may be sterilized by filtration, γ-irradiation and autoclaving.

What is claimed is:

1. A method of delivering an agent to the lymph nodes of an animal by intravascular administration, the method comprising intravascularly administering to the animal a composition comprising (i) an organic inner core incorporating said agent, and (ii) an outer carbohydrate structure comprising a plurality of carbohydrate molecules grafted to said inner core; and allowing sufficient time for said composition to accumulate within the lymph nodes of the animal, wherein said composition has sufficient preference for lymph node tissue over liver tissue in a rat such that, 24 hours after intravascular injection of a dosage of 1 mg/kg body weight, the accumulated dose percent per gram of paraaortic and mesenteric lymph node tissue is greater than the accumulated dose percent per gram of liver tissue.

2. A method of claim 1, wherein said carbohydrate structure sterically protects said inner core and said agent once said composition is administered to the animal.

3. A method of claim 1, wherein said organic inner core comprises one or more polymeric molecules.

4. A method of claim 3, wherein said polymeric molecule consists essentially of a polypeptide, polysaccharide, polyester, or polyamide, or a copolymer of any two or more peptides, saccharides, esters, or amides.

5. A method of claim 3, wherein said polymeric molecule comprises polylysine.

6. A method of claim 1, wherein said outer carbohydrate structure is diffuse and allows entry of small molecules.

7. A method of claim 1, wherein said agent comprises a detectable label.

8. A method of claim 7, wherein said detectable label is a magnetic, superparamagnetic, radiopaque, or radioactive substance.

9. A method of claim 1, wherein said agent comprises a therapeutic substance.

10. A method of claim 1, wherein said carbohydrate molecules are dextran, starch, glucose, nonionic synthetic polymers of sucrose, or their derivatives or analogs.

11. A composition that accumulates in the lymph nodes of an animal after intravascular administration, the composition comprising (i) an organic inner core, and (ii) an outer carbohydrate structure comprising a plurality of carbohydrate molecules grafted to said inner core, wherein said composition has sufficient preference for lymph node tissue over liver tissue in a rat such that, 24 hours after intravascular injection of a dosage of 1 mg/kg body weight, the accumulated dose percent per gram of paraaortic and mesenteric lymph node tissue is greater than the accumulated dose percent per gram of liver tissue.

12. A composition of claim 11, wherein said carbohydrate structure sterically protects said inner core once said composition is administered to the animal.

13. A composition of claim 11, wherein said carbohydrate molecules each have a molecular weight of 1 to 20 kDa.

14. A composition of claim 11, wherein said inner core comprises one or more polymeric molecules.

15. A composition of claim 14, wherein said polymeric molecule consists essentially of a polypeptide, polysaccharide, polyester, or polyamide, or a copolymer of any two or more peptides, saccharides, esters, or amides.

16. A composition of claim 14, wherein said polymeric molecule comprises polylysine.

17. A composition of claim 11, further comprising an agent incorporated into said organic inner core.

18. A composition of claim 17, wherein said agent comprises a detectable label.

19. A method of imaging the lymph nodes of an animal, said method comprising intravascularly injecting a composition of claim 18 into the animal, allowing sufficient time for said composition to accumulate within the lymph nodes of the animal, and detecting the presence of said composition in the lymph nodes of the animal, thereby imaging the lymph nodes of the animal.

20. A composition of claim 18, wherein said detectable label is a magnetic, superparamagnetic, radiopaque, or radioactive substance.

21. A composition of claim 17, wherein said agent comprises a therapeutic substance.

22. A composition of claim 11, wherein said carbohydrate molecules are dextran, starch, glucose, nonionic synthetic polymers of sucrose, or their derivatives or analogs.

23. A composition that accumulates in the lymph nodes of an animal after intravascular administration, the composition comprising (i) an inner core comprising one or more colloidal iron oxide particles, and (ii) a dense, outer carbohydrate structure comprising a plurality of carbohydrate molecules grafted to said inner core, said carbohydrate structure sterically protecting said inner core once said composition is administered to the animal, wherein said outer carbohydrate layer is grafted to said inner core during core formation by dissolving an iron salt in a solution of at least 5 percent, by weight, of said carbohydrate in water, cooling the resulting solution to about 4° C., increasing the pH of the cooled solution to about 10.0, incubating the solution at about 70° C., and separating said composition from the solution, and wherein said composition has sufficient preference for lymph node tissue over liver tissue in a rat such that, 24 hours after intravascular injection of a dosage of 1 mg/kg body weight, the accumulated dose percent per gram of paraaortic and mesenteric lymph node tissue is greater than the accumulated dose percent per gram of liver tissue.

24. A method of imaging the lymph nodes of an animal, said method comprising intravascularly injecting a composition of claim 23 into the animal, allowing sufficient time for said composition to accumulate within the lymph nodes of the animal, and detecting the presence of said composition in the lymph nodes of the animal, thereby imaging the lymph nodes of the animal.

25. A composition of claim 23, wherein said iron salt is a salt of $Fe^{2+}$ or $Fe^{3+}$.

26. A composition of claim 23, further comprising an agent incorporated into said inner core.

27. A method of delivering an agent to the lymph nodes of an animal by intravascular administration, the method comprising intravascularly administering to the animal a composition of claim 26; and allowing sufficient time for said composition to accumulate within the lymph nodes of the animal.

28. A composition that accumulates in the lymph nodes of an animal after intravascular administration, the composition comprising (i) an inner core comprising one or more diamagnetic or paramagnetic colloidal particles, and (ii) a dense, outer carbohydrate structure comprising a plurality of carbohydrate molecules grafted to said inner core, wherein said composition has sufficient preference for lymph node tissue over liver tissue in a rat such that, 24 hours after intravascular injection of a dosage of 1 mg/kg body weight, the accumulated dose percent per gram of paraaortic and mesenteric lymph node tissue is greater than the accumulated dose percent per gram of liver tissue.

29. A method of imaging the lymph nodes of an animal, said method comprising intravascularly injecting a composition of claim 28 into the animal, allowing sufficient time for said composition to accumulate within the lymph nodes of the animal, and detecting the presence of said composition in the lymph nodes of the animal, thereby imaging the lymph nodes of the animal.

30. A composition of claim 28, wherein said carbohydrate molecules are dextran, starch, glucose, nonionic synthetic polymers of sucrose, or their derivatives or analogs.

31. A composition of claim 28, wherein said carbohydrate molecules each have a molecular weight of 1 to 20 kDa.

32. A composition of claim 28, further comprising an agent incorporated into said inner core.

33. A method of delivering an agent to the lymph nodes of an animal by intravascular administration, the method comprising intravascularly administering to the animal a composition of claim 32; and allowing sufficient time for said composition to accumulate within the lymph nodes of the animal.

34. A composition of claim 32, wherein said agent comprises a therapeutic substance.

35. A composition of claim 28, wherein said paramagnetic particle comprises gadolinium, manganese, or dysprosium.

36. A composition of claim 28, wherein said diamagnetic particle comprises indium.

* * * * *